US011850152B2

(12) United States Patent
Shuey et al.

(10) Patent No.: US 11,850,152 B2
(45) Date of Patent: Dec. 26, 2023

(54) DEVICES, SYSTEMS, AND METHODS FOR ARTIFICIAL CHORDAE TENDINEAE

(71) Applicant: Boston Scientific Scimed, Inc., Maple Grove, MN (US)

(72) Inventors: Daniel Shuey, Pine City, MN (US); Joel T. Eggert, Plymouth, MN (US); James P. Rohl, Prescott, WI (US); Aaron Abbott, Columbia Hieghts, MN (US); Christopher J. Koudela, New London, MN (US); Brian Kennedy, Mora, MN (US); Joseph Walker, Shoreview, MN (US); Douglas Pennington, Stillwater, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 707 days.

(21) Appl. No.: 16/919,806

(22) Filed: Jul. 2, 2020

(65) Prior Publication Data
US 2021/0000599 A1   Jan. 7, 2021

Related U.S. Application Data

(60) Provisional application No. 62/873,352, filed on Jul. 12, 2019, provisional application No. 62/873,354, (Continued)

(51) Int. Cl.
*A61F 2/24* (2006.01)
*A61B 17/00* (2006.01)
(Continued)

(52) U.S. Cl.
CPC .......... *A61F 2/2457* (2013.01); *A61F 2/2463* (2013.01); *A61F 2/2466* (2013.01);
(Continued)

(58) Field of Classification Search
CPC .... A61F 2/2457; A61F 2/2463; A61F 2/2466; A61F 2/2487; A61F 2220/0008;
(Continued)

(56) References Cited

U.S. PATENT DOCUMENTS 5,797,933 A * 8/1998 Snow ............... A61B 17/12109
606/198
7,736,388 B2   6/2010 Goldfarb et al.
(Continued)

OTHER PUBLICATIONS

International Search Report and Written Opinion for the International Patent Application No. PCT/US2020/040693, dated Oct. 23, 2020, 14 pages.

*Primary Examiner* — Suzette J Gherbi
(74) *Attorney, Agent, or Firm* — Seager, Tufte & Wickhem, LLP

(57) ABSTRACT

The present disclosure relates generally to the field of medical devices for treating heart disease. In particular, the present disclosure relates to medical devices, systems, and methods for delivering artificial chordae tendineae in a patient. A system for delivering a chordae tendineae into a heart may include a delivery catheter. A clamp catheter may be configured to translate through the delivery catheter. A spreader may be disposed on the clamp catheter. A first clamp may be at least partially contained in the spreader in a closed configuration and may be attached to the chordae tendineae. An anchor catheter may be configured to translate through the delivery catheter and may have an anchor attached to the chordae tendineae. A sheath may be extended over the anchor catheter and anchor and may be configured to restrain an arm of the anchor.

20 Claims, 22 Drawing Sheets

Related U.S. Application Data filed on Jul. 12, 2019, provisional application No. 62/873,357, filed on Jul. 12, 2019, provisional application No. 62/870,343, filed on Jul. 3, 2019.

(51) Int. Cl.
| | | |
|---|---|---|
| *A61B 8/08* | (2006.01) | |
| *A61B 8/12* | (2006.01) | |
| *A61B 6/00* | (2006.01) | |
| *A61M 25/00* | (2006.01) | |

(52) U.S. Cl.
CPC .......... *A61F 2/2487* (2013.01); *A61B 6/487* (2013.01); *A61B 6/503* (2013.01); *A61B 8/0883* (2013.01); *A61B 8/12* (2013.01); *A61B 2017/00407* (2013.01); *A61F 2220/0008* (2013.01); *A61F 2220/0075* (2013.01); *A61M 2025/0004* (2013.01)

(58) Field of Classification Search
CPC . A61F 2220/0075; A61B 6/487; A61B 6/503; A61B 8/0883; A61B 8/12; A61B 2017/00407; A61M 2025/0004
See application file for complete search history.

(56) References Cited

U.S. PATENT DOCUMENTS

| | | | |
|---|---|---|---|
| 8,252,050 | B2 | 8/2012 | Maisano et al. |
| 9,681,864 | B1 | 6/2017 | Gammie et al. |
| 10,136,993 | B1 | 11/2018 | Metchik et al. |
| 2007/0118151 | A1 | 5/2007 | Davidson |
| 2009/0105729 | A1 | 4/2009 | Zentgraf |
| 2011/0060407 | A1* | 3/2011 | Ketai ................. A61F 2/2463 623/2.37 |
| 2012/0184971 | A1* | 7/2012 | Zentgraf ............ A61B 17/0469 606/139 |
| 2013/0231735 | A1* | 9/2013 | Deem ................. A61F 2/2436 623/2.11 |
| 2015/0250590 | A1 | 9/2015 | Gries et al. |
| 2017/0245993 | A1 | 8/2017 | Gross et al. |
| 2017/0252032 | A1 | 9/2017 | Hiorth et al. |
| 2017/0290589 | A1* | 10/2017 | Wilson ................ A61F 6/206 |
| 2018/0185153 | A1 | 7/2018 | Bishop et al. |
| 2018/0250133 | A1 | 9/2018 | Reich et al. |
| 2018/0303614 | A1 | 10/2018 | Schaffner et al. |
| 2020/0405485 | A1* | 12/2020 | Rohl ................... A61F 2/2466 |
| 2021/0007847 | A1* | 1/2021 | Eggert ................ A61F 2/2457 |
| 2022/0117734 | A1* | 4/2022 | Hiorth ............... A61B 17/0469 |
| 2022/0125587 | A1* | 4/2022 | Hou .................... A61F 2/2436 |

\* cited by examiner

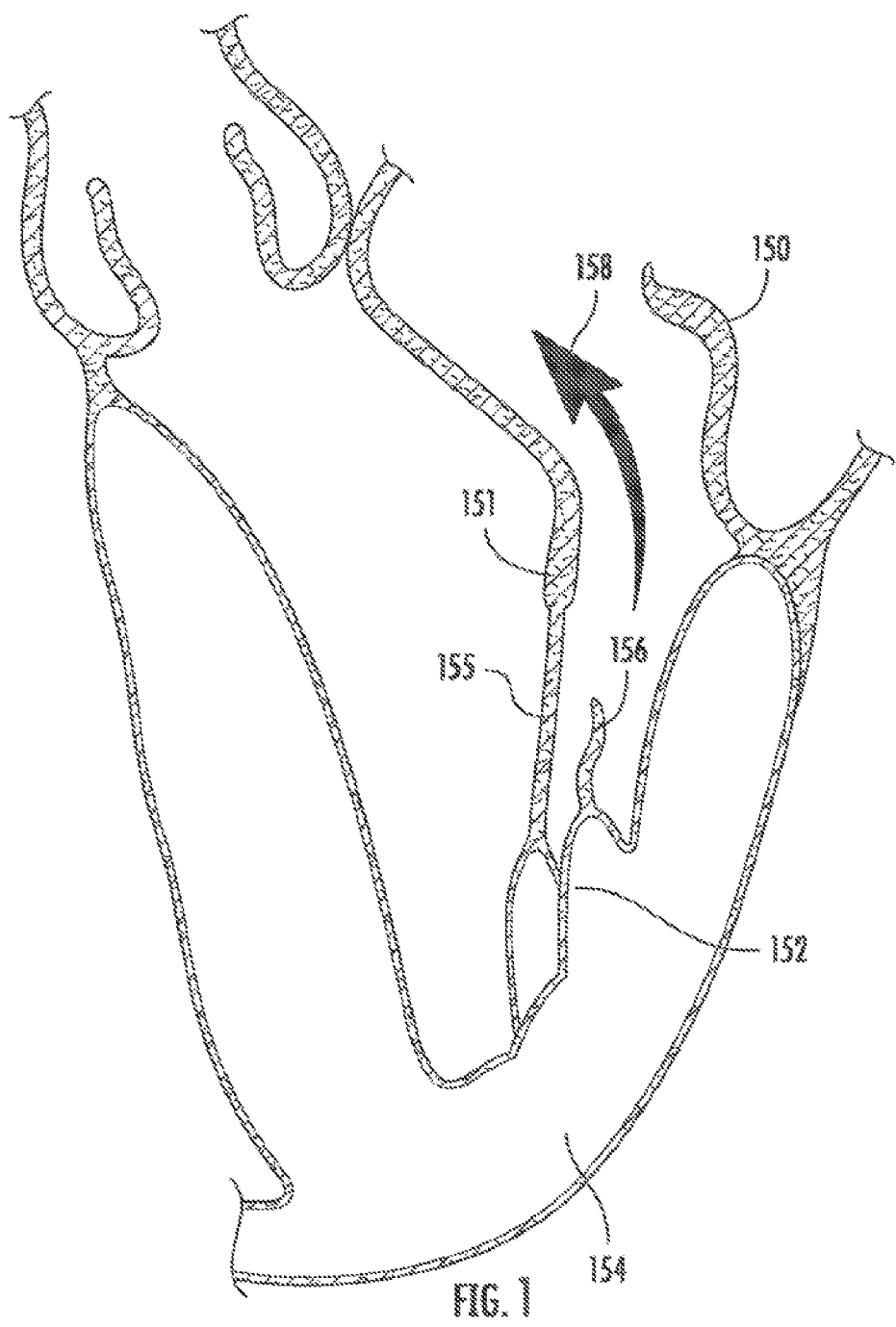

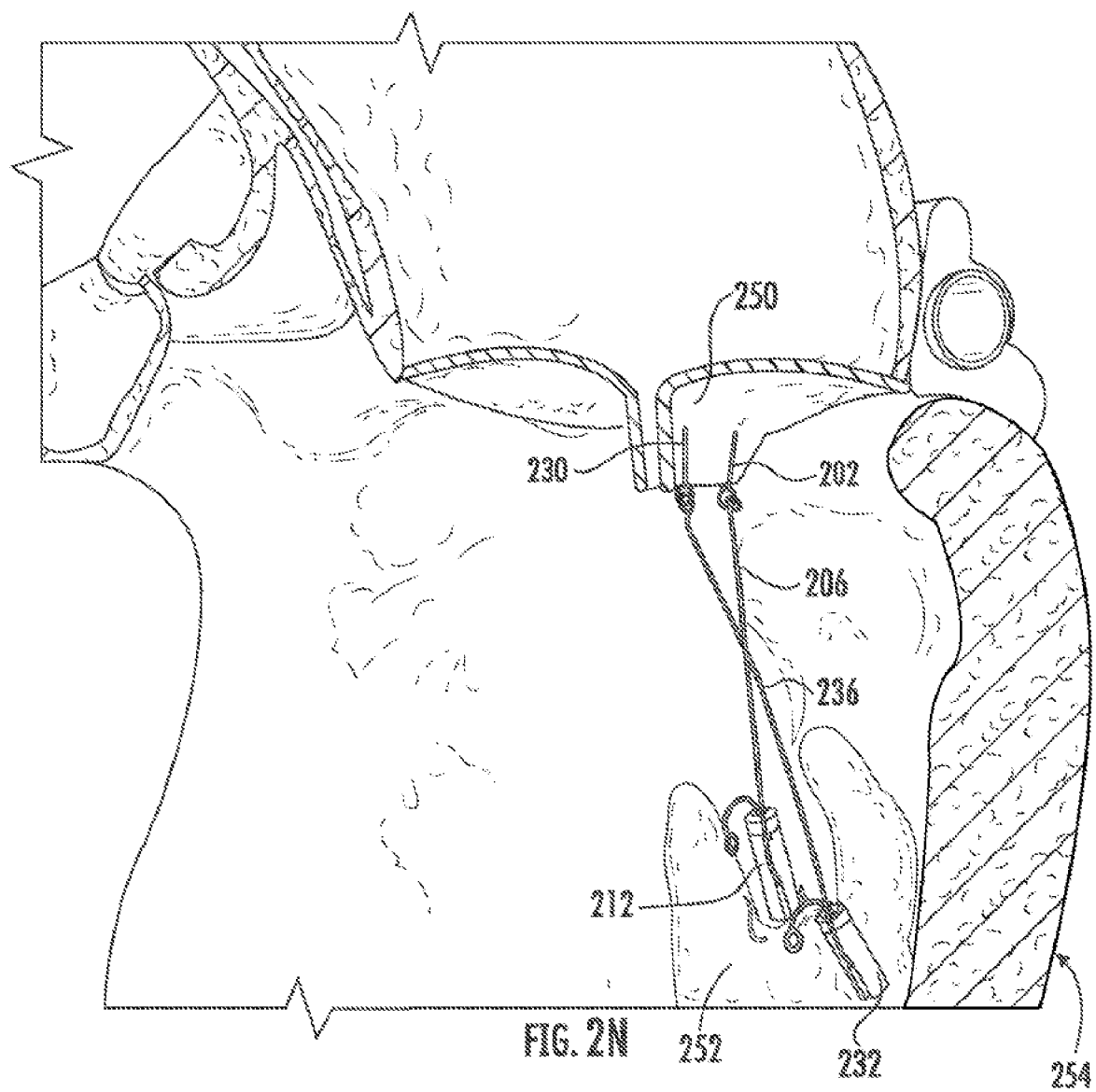

DEVICES, SYSTEMS, AND METHODS FOR ARTIFICIAL CHORDAE TENDINEAE

CROSS-REFERENCE TO RELATED APPLICATIONS

The present application claims the benefit of priority under 35 U.S.C. § 119 to U.S. Provisional Patent Application 62/873,357, filed on Jul. 12, 2019; U.S. Provisional Patent Application 62/873,352, filed Jul. 12, 2019; U.S. Provisional Patent Application 62/873,354, filed Jul. 12, 2019; and U.S. Provisional Patent Application 62/870,343, filed Jul. 3, 2019, which applications are incorporated herein by reference in their entireties for all purposes.

FIELD

The present disclosure relates generally to the field of medical devices for treating heart disease. In particular, the present disclosure relates to medical devices, systems, and methods for delivering artificial chordae tendineae in a patient.

BACKGROUND

In a healthy heart, chordae tendineae connect papillary muscles to heart valve leaflets to control opening and closing of the heart valve during systole and diastole. As a heart disease progresses, the chordae tendineae may stretch inelastically and may rupture. A stretched and/or ruptured chordae tendineae may result in a flailing leaflet that may no longer have capacity to form a valving seal for normal heart function. Abnormal blood flow regurgitation may develop, preventing adequate blood supply through cardiovascular systems.

Mitral valve disease is typically repaired via invasive surgical intervention or by pinching of the leaflets together creating dual, smaller openings, or a mitral valve replacement of the native valve. These and other approaches may accompany risky by-pass surgery that may include an opening into the patient's chest and heart chamber to expose the mitral valve for direct viewing and repair. Thus, transluminal solutions to mitral valve disease are needed.

A variety of advantageous medical outcomes may be realized by the medical devices, systems, and methods of the present disclosure, which include delivering artificial chordae tendineae in a patient.

SUMMARY

Embodiments of the present disclosure may assist generally with delivering artificial chordae tendineae in a patient. In one aspect, a system for delivering a chordae tendineae into a heart of a patient may include a delivery catheter. A clamp catheter may be configured to translate through the delivery catheter. A spreader may be disposed on the clamp catheter. A first clamp may be at least partially contained in the spreader in a closed configuration. The first clamp may be attached to a first end of the chordae tendineae. An anchor catheter may be configured to translate through the delivery catheter. The anchor catheter may have an anchor attached to a second end of the chordae tendineae. A sheath may be extended over the anchor catheter and anchor. The sheath may be configured to restrain an arm of the anchor.

In various embodiments described here or otherwise, the second end of the chordae tendineae may extend through a ratchet of the anchor. The second end of the chordae tendineae may be coupled to a tether extending through the anchor catheter. The tether may be configured to increase a tension in the chordae tendineae via a translation of the tether. A release filament may extend through a release roller of the ratchet. The release filament may be configured to unlock the chordae tendineae from the ratchet via translation of the release filament. The first clamp may be reversibly locked to the spreader. A second clamp may be attached to the first clamp by a clamp filament. The clamp filament may be slidably coupled to the first end of the chordae tendineae. The anchor catheter and sheath may extend through the clamp catheter. The clamp may include a plurality of clamp arms at a first end. The plurality of clamp arms may have a closed configuration in which the clamp arms are oriented toward each other, and an open configuration in which the clamp arms are oriented away from each other. A spring portion may be coupled to the plurality of clamp arms at a second end. The spring portion may be configured to bias the clamp arms to the closed configuration. The clamp arms of the clamp may be configured to fixedly engage with a leaflet of a heart valve. The first spreader may include a base disposed on the clamp catheter. A pin may extend from the base. A lever may be rotatably disposed about the pin. A first channel may extend through the base substantially parallel with a first aperture of one of the plurality of clamp arms and may be configured to accept one of the plurality of clamp arms. A second channel may extend through the lever substantially parallel with a second aperture of one of the plurality of arms and may be configured to accept one of the plurality of arms. A first filament may extend from the lever. The filament may be configured to move the lever and the clamp between the closed configuration and the open configuration. A first pin may be disposed within the first aperture and the first channel. A second pin may be disposed within the second aperture and the second channel. A shape-memory of the arm of the anchor of the anchor catheter may be configured to bias the arm to puncture through a muscle and may extend proximally as the arm transitions from a restrained configuration toward a neutral configuration. The anchor catheter may be disposed within the sheath. The sheath may be disposed within the clamp catheter. The clamp catheter may be disposed within the delivery catheter. A handle may be coupled to the delivery catheter, the clamp catheter, the anchor catheter, and the sheath, and configured to allow a medical professional to selectively and independently translate the delivery catheter, the clamp catheter, the anchor catheter, and the sheath. A second spreader may be disposed on the clamp catheter substantially opposing the first spreader. The anchor may be attached to the anchor catheter by interlocking screw threads. The sheath may be configured to restrain the arm such that the arm is extended distally.

In various embodiments, a method of delivering a chordae tendineae into a heart of a patient may include transluminally inserting a delivery catheter into the heart. A clamp catheter may be extended through the delivery catheter. The clamp catheter may have a spreader containing a clamp in a closed configuration. The clamp may be attached to a first end of the chordae tendineae. The spreader may be manipulated to transition the clamp from the closed configuration to an open configuration. The clamp may be positioned adjacent a leaflet of a valve of the heart. The spreader may be manipulated to transition the clamp from the open configuration to the closed configuration onto the leaflet. A sheath may be extended through the delivery catheter towards a tissue of the heart. An anchor catheter having an anchor may be extended, the anchor being attached to a second end of the chordae tendineae at a distal end of the anchor catheter through the sheath. The anchor may be driven into the tissue.

In various embodiments described here or otherwise, regurgitation of the valve may be observed via transesophageal echocardiogram or fluoroscopy and adjusting a tension in the chordae tendineae. A tension in the chordae tendineae may be adjusted by selectively translating the chordae tendineae through a ratchet of the anchor and selectively releasing the chordae tendineae from the ratchet. The clamp may be deployed from the spreader by removing a plurality of pins from the clamp and spreader. Manipulating the spreader may be performed by translating a spreader filament proximally through the clamp catheter. The clamp may be repositioned by transitioning the clamp from the closed configuration to the open configuration, moving the clamp from a first portion of the leaflet to a second portion of the leaflet, and transitioning the clamp from the open configuration to the closed configuration onto the leaflet. The sheath extended through the delivery catheter may be extended through the clamp catheter. Driving the anchor may include deploying an arm from the anchor by extending the anchor catheter such that the arm extends at least partially out of a distal end of the sheath. The anchor may be repositioned by extending the anchor catheter proximally through the sheath from a first portion of the tissue and extending the anchor catheter to a second portion of the tissue. The clamp catheter, the sheath, the anchor catheter, and the delivery catheter may be removed from the patient.

In an aspect, a method of delivering an chordae tendineae into a heart of a patient may include delivering a clamp onto a leaflet of a heart valve. The clamp may be attached to a first end of the chordae tendineae. An anchor may be delivered into a muscle of the heart. The anchor may be attached to a second end of chordae tendineae. A tension may be adjusted in the chordae tendineae. Delivering the clamp may further comprise manipulating a spreader containing the clamp in a closed configuration to transition the clamp from the closed configuration to an open configuration, positioning the clamp adjacent the leaflet, and manipulating the spreader to transition the clamp from the open configuration to the closed configuration onto the leaflet.

In various embodiments, delivering the anchor may include deploying a plurality of arms into the muscle from the anchor by extending the anchor such that the arms extend at least partially out of a distal end of a sheath. Regurgitation of the heart valve may be observed via transesophageal echocardiogram or fluoroscopy.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIG. 1 illustrates a cross-sectional view of flailing leaflet of a mitral valve during blood flow regurgitation.

FIG. 2J illustrates a cross-sectional view of the heart of FIGS. 2A-2I with a release filament being withdrawn from the anchor.

FIG. 2N illustrates a cross-sectional view of the heart of FIGS. 2A-2M with the additional artificial chordae tendineae delivered.

DETAILED DESCRIPTION

Figure 2A:
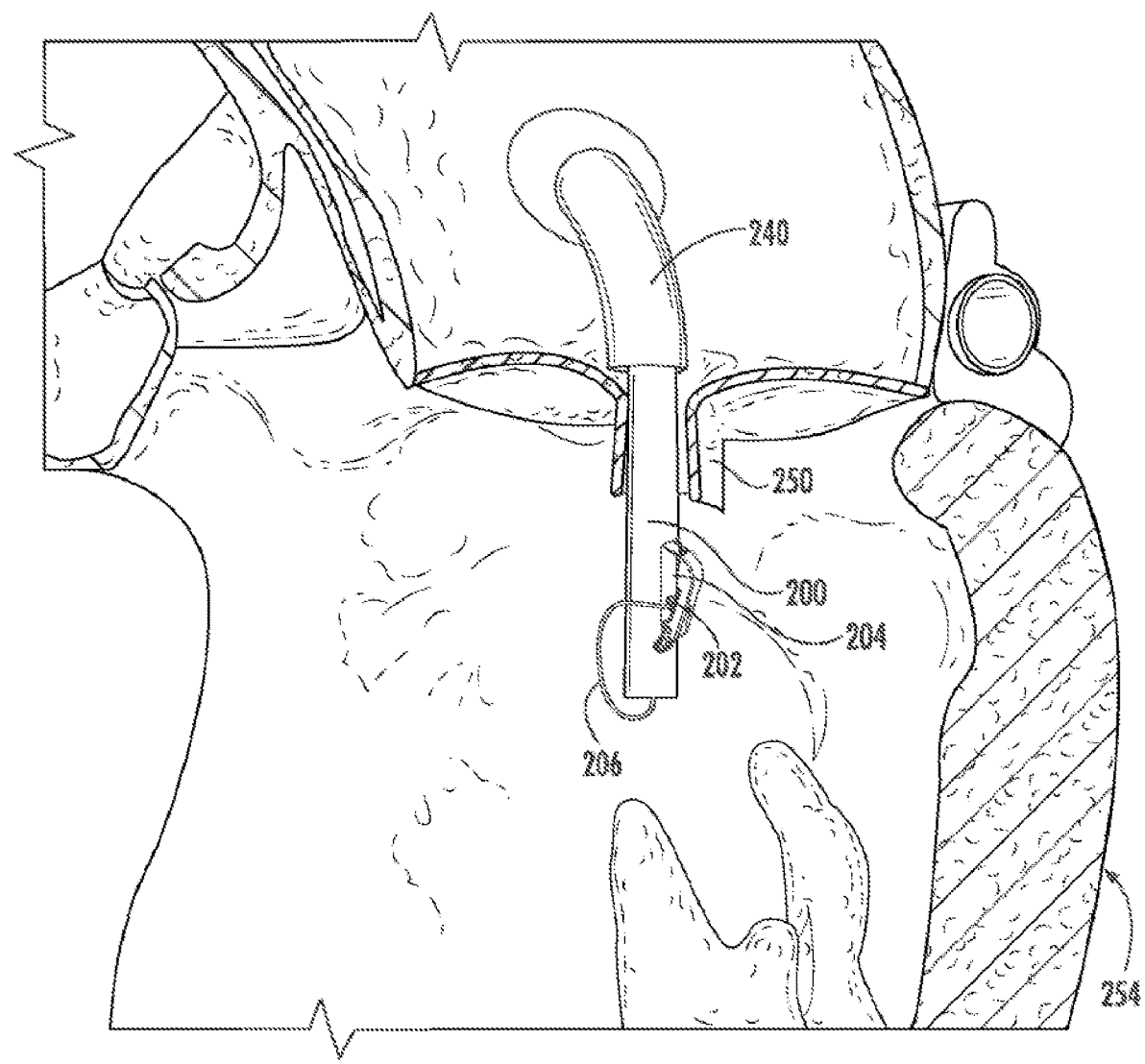
FIG. 2A illustrates a cross-sectional view of a heart and extending a clamp catheter into the heart, according to an embodiment of the present disclosure.

The present disclosure is not limited to the particular embodiments described. The terminology used herein is for the purpose of describing particular embodiments only and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure may be described with specific reference to medical devices and systems (e.g., transluminal devices inserted through a femoral vein or the like) for selective access to a heart valve, it should be appreciated that such medical devices and systems may be used in a variety of medical procedures that involve clamping a leaflet of a valve or clamping a tissue wall. The disclosed medical devices and systems may also be inserted via different access points and approaches, e.g., percutaneously, endoscopically, laparoscopically, or combinations thereof.

As used herein, the singular forms "a," "an," and "the" are intended to include the plural forms as well, unless the context clearly indicates otherwise. The terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

As used herein, "proximal end" refers to the end of a device that lies closest to the medical professional along the device when introducing the device into a patient, and "distal end" refers to the end of a device or object that lies furthest from the medical professional along the device during implantation, positioning, or delivery.

As used herein, the conjunction "and" includes each of the structures, components, features, or the like, which are so conjoined, unless the context clearly indicates otherwise, and the conjunction "or" includes one or the others of the structures, components, features, or the like, which are so conjoined, singly and in any combination and number, unless the context clearly indicates otherwise.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified. The recitation of numerical ranges by endpoints includes all numbers within that range, including the endpoints (e.g. 1 to 5 includes 1, 1.5, 2, 2.75, 3, 3.80, 4, and 5).

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

Heart disease including atrioventricular heart valve malfunctions impede patient cardiac output, which reduces patient quality of life and lifespan. With reference to a heart 154 illustrated in FIG. 1, as heart disease progresses, the chordae tendineae 155 that connect the papillary muscle 152 to a valve leaflet 151 may stretch inelastically and may rupture. A stretched and/or ruptured chordae tendineae 156 may result in a flailing leaflet 150 that may no longer have capacity to form a valving seal for normal heart function. For example, abnormal blood flow regurgitation in the direction of vector 158 may develop. Regurgitation prevents an adequate supply of blood to be delivered through the cardiovascular systems.

Repositioning, repair, and/or replacement of one or more leaflets of a valve and/or chordae tendinea may be desirable to treat heart disease. The devices, systems, and methods of the present disclosure may be used alone or together with other devices, systems, and methods to treat heart disease. Examples of devices, systems, and methods with which embodiments of the present disclosure may be implemented include, but are not limited to, those described in U.S. Patent Application Publication No. 2021/0000597, filed on Jul. 2, 2020, and titled Devices, Systems, and Methods for Adjustably Tensioning an Artificial Chordae Tendineae Between a Leaflet and a Papillary Muscle or Heart Wall; U.S. patent Application Publication No. 2021/0007847, filed on Jul. 2, 2020, and titled Devices, Systems, And Methods For Clamping A Leaflet Of A Heart Valve; U.S. Patent Application Publication No. 2021/0000598, filed on Jul. 2, 2020 and titled Devices, Systems, and Methods for Anchoring an Artificial Chordae Tendineae to a Papillary Muscle or Heart Wall, which applications are hereby incorporated by reference herein in their entireties and for all purposes. each of which is filed on even date herewith and each of which is herein incorporated by reference in its entirety and for all purposes. Examples of devices described therein may be modified to incorporate embodiments or one or more features of the present disclosure.

With reference to FIG. 2A, an embodiment of a method of delivering a chordae tendineae 206 according to an embodiment of the present disclosure is illustrated including a delivery catheter 240 extended through an inferior vena cava, through a septum, and into the left atrium of a heart 254. A clamp catheter 200 is extended distally through the delivery catheter 240 through the leaflets 250. The clamp catheter 200 has a spreader 204 disposed on a distal end of the clamp catheter 200. The spreader 204 contains a clamp 202 in a closed configuration. An artificial chordae tendineae 206 has a first end attached to the clamp 202 and another end of the artificial chordae tendineae 206 extends proximally into the clamp catheter 200. The clamp catheter 200 extends proximally through the leaflets 250 into the delivery catheter 240. The spreader 204 and the clamp 202 are in the closed configuration such that the spreader 204 and clamp 202 maintain a lower profile than in the open configuration to prevent undesirable friction with the delivery catheter 240 and surrounding anatomy as the clamp catheter 200 is translated through the delivery catheter 240 and through the body.

Figure 2B:
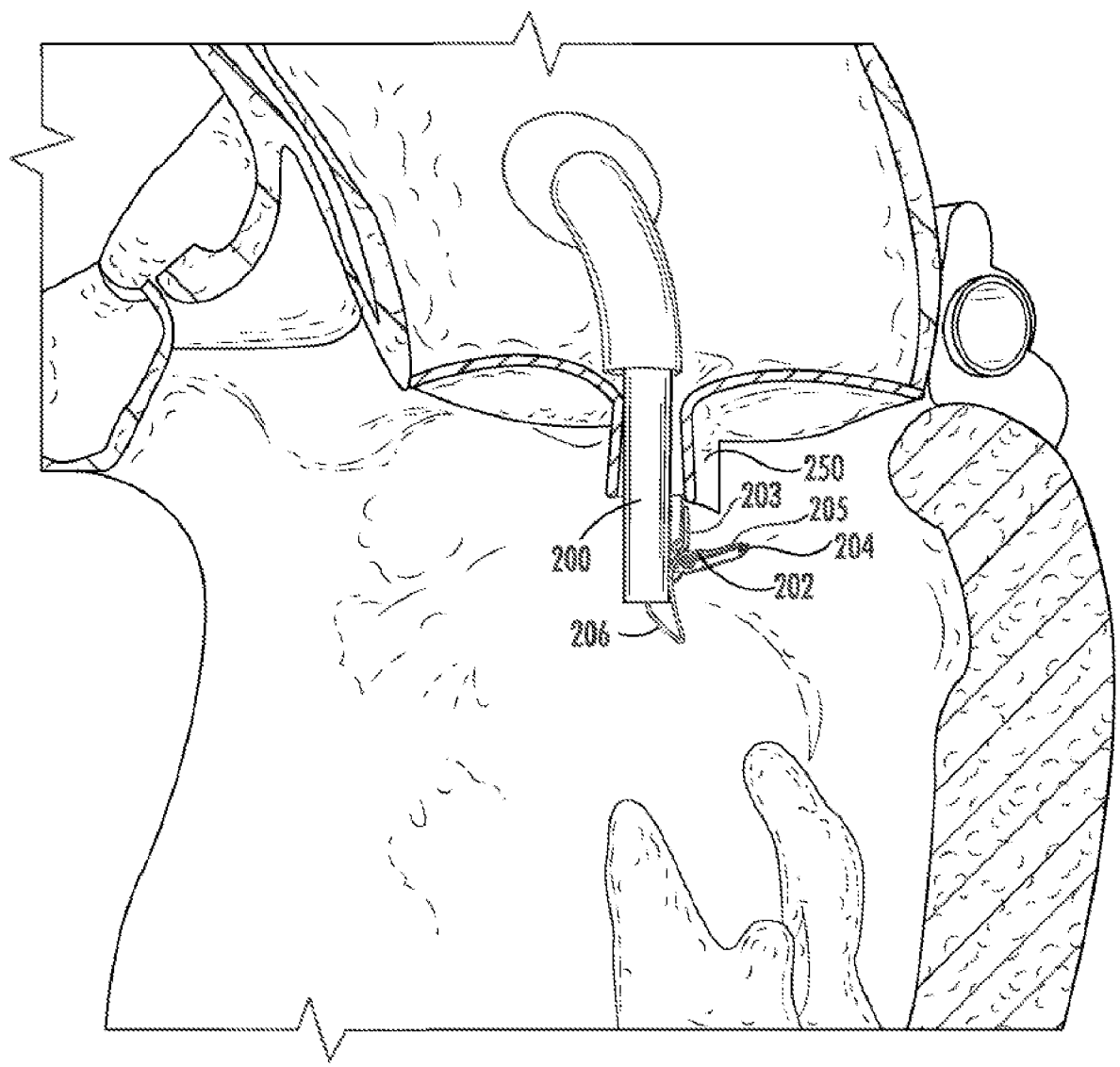
FIG. 2B illustrates a cross-sectional view of the heart of FIG. 2A and transitioning a clamp of the clamp catheter to an open configuration.
Figure 6:
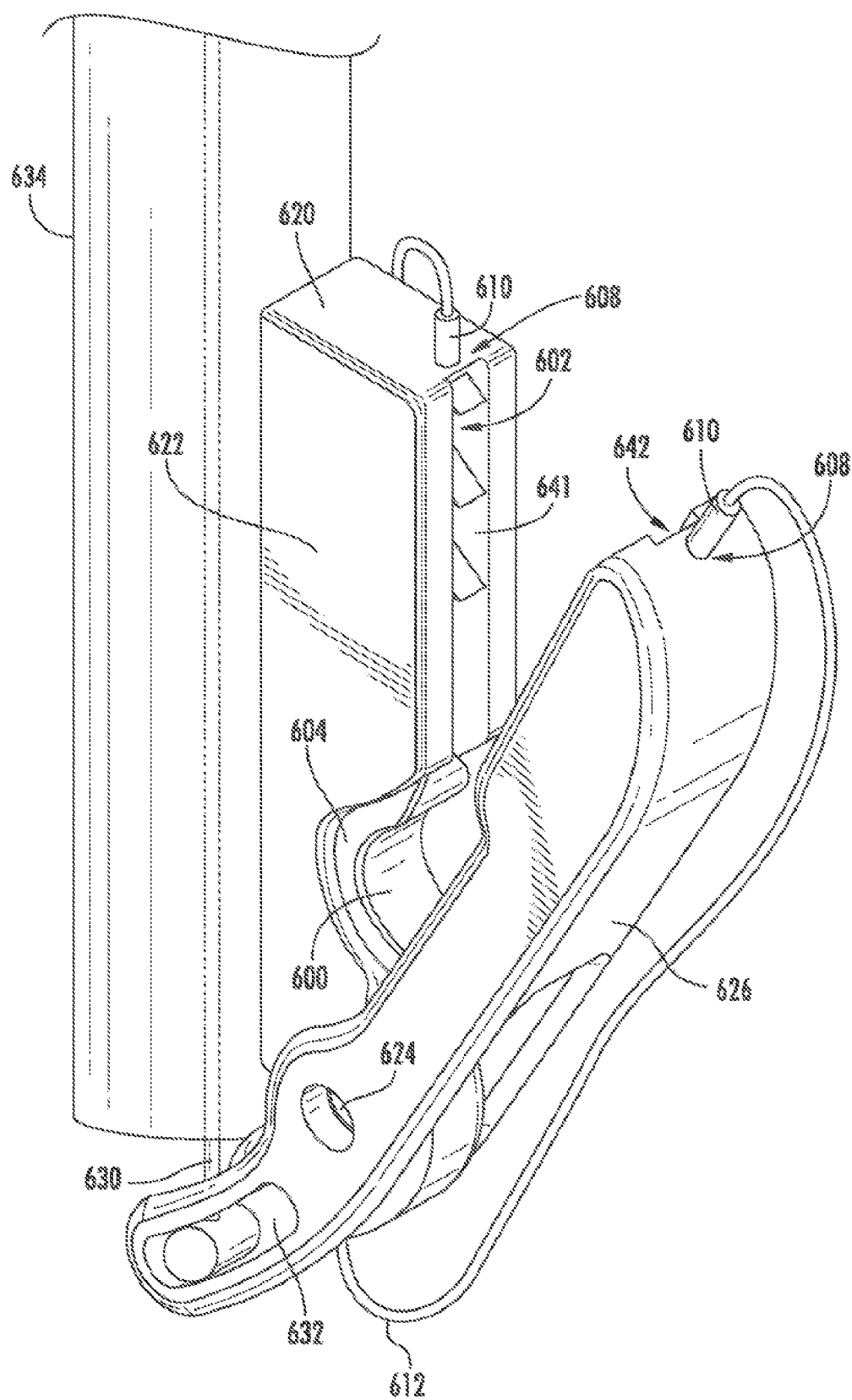
FIG. 6 illustrates a perspective view of a spreader disposed on a catheter in an open configuration, according to an embodiment of the present disclosure.

With reference to FIG. 2B, the spreader 204 may be manipulated to transition the clamp 202 from the closed configuration to the open configuration by, for example, proximally translating a filament, such as illustrated and described with respect to FIG. 6 herein, through the clamp catheter 200 that is attached to a lever of the spreader 204 to open the spreader 204, while releasing the filament may allow a spring portion of the clamp 202 to close the lever of the spreader 204. The clamp catheter 200 may be oriented such that the open clamp 202 is positioned adjacent to a leaflet 250 to accept the leaflet 250 between two arms 203, 205 of the clamp 202. The clamp catheter 200 may be rotated and/or translated proximally or distally to position the clamp 202 about the leaflet 250. For example, a middle of a posterior leaflet may be flailing, and a clamp may be delivered on the flailing portion of the leaflet, adjacent to the flailing portion of the leaflet, and/or on either side of the flailing portion.

Figure 2C:
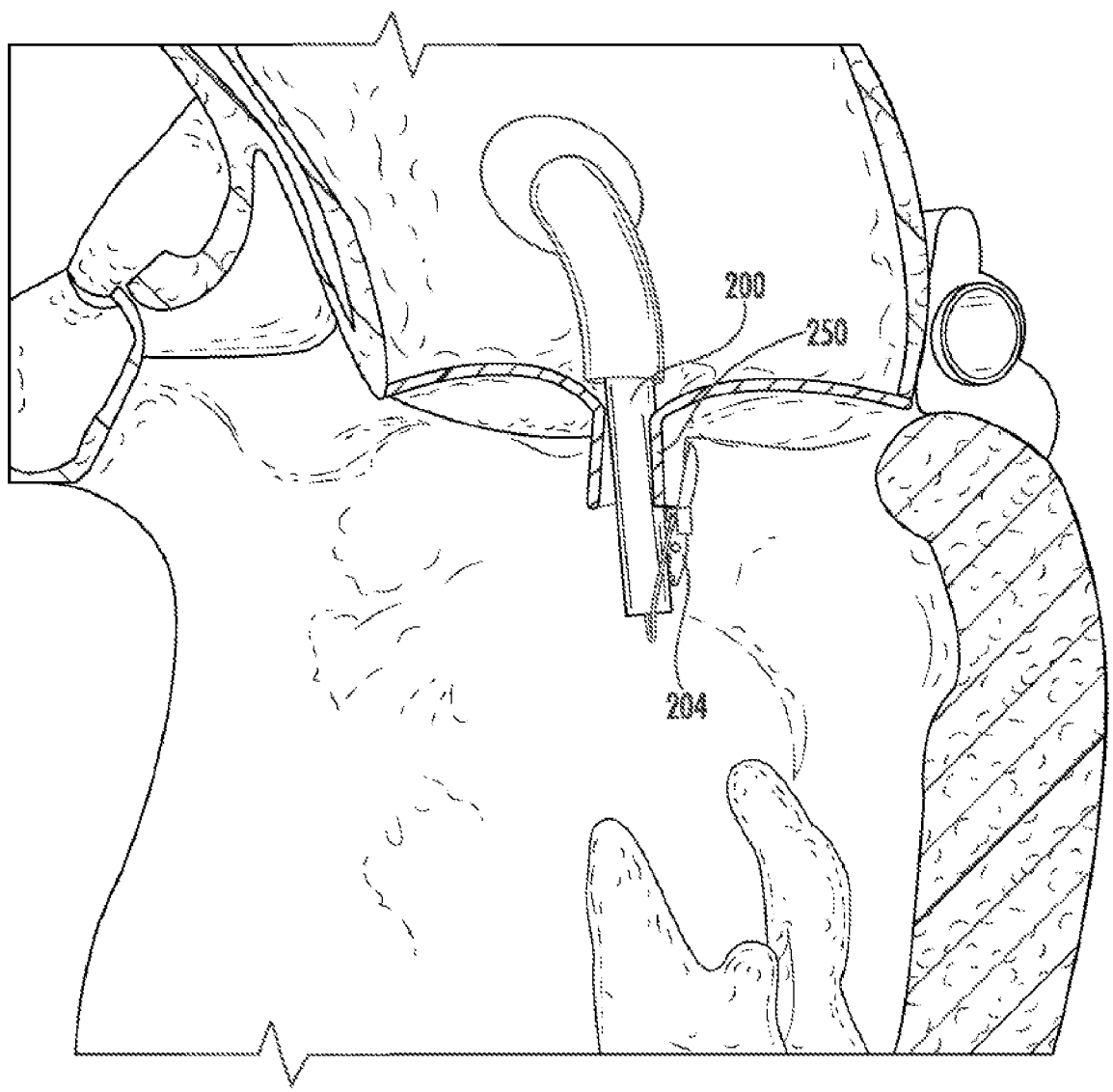
FIG. 2C illustrates a cross-sectional view of the heart of FIGS. 2A and 2B and transitioning the clamp to a closed configuration.

With reference to FIG. 2C, the spreader 204 may be manipulated (e.g., via a handle as discussed herein) to transition the clamp 202 from the open configuration to the closed configuration onto the leaflet 250. Because the clamp 202 is fixed to the spreader 204, the spreader 204 may be further manipulated to transition the clamp 202 from the closed configuration on the leaflet 250 to the open configuration for repositioning the clamp 202 on the leaflet 250.

Figure 2D:
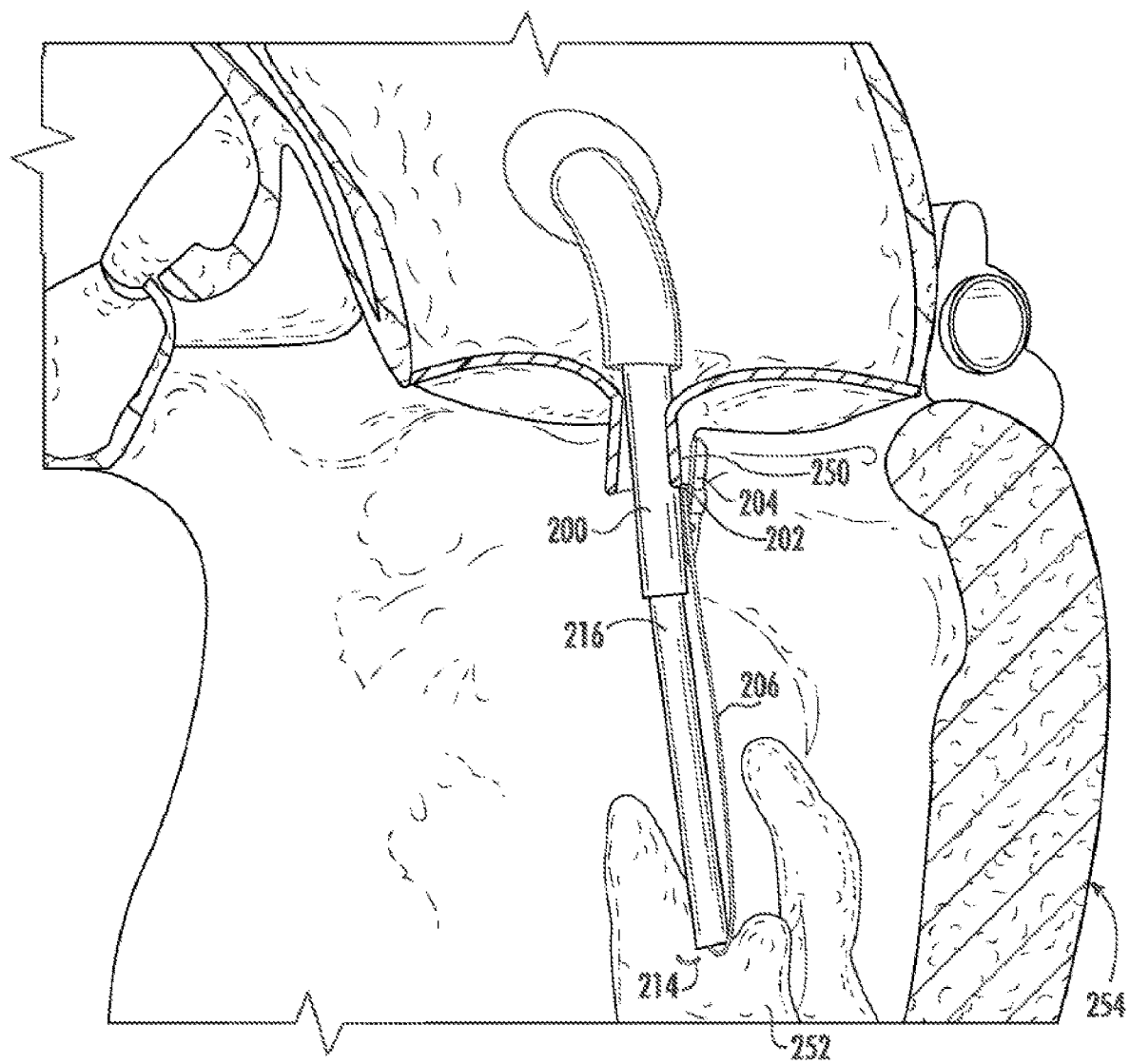
FIG. 2D illustrates a cross-sectional view of the heart of FIGS. 2A-2C and partially deploying arms of an anchor into tissue of the hear.
Figure 2E:
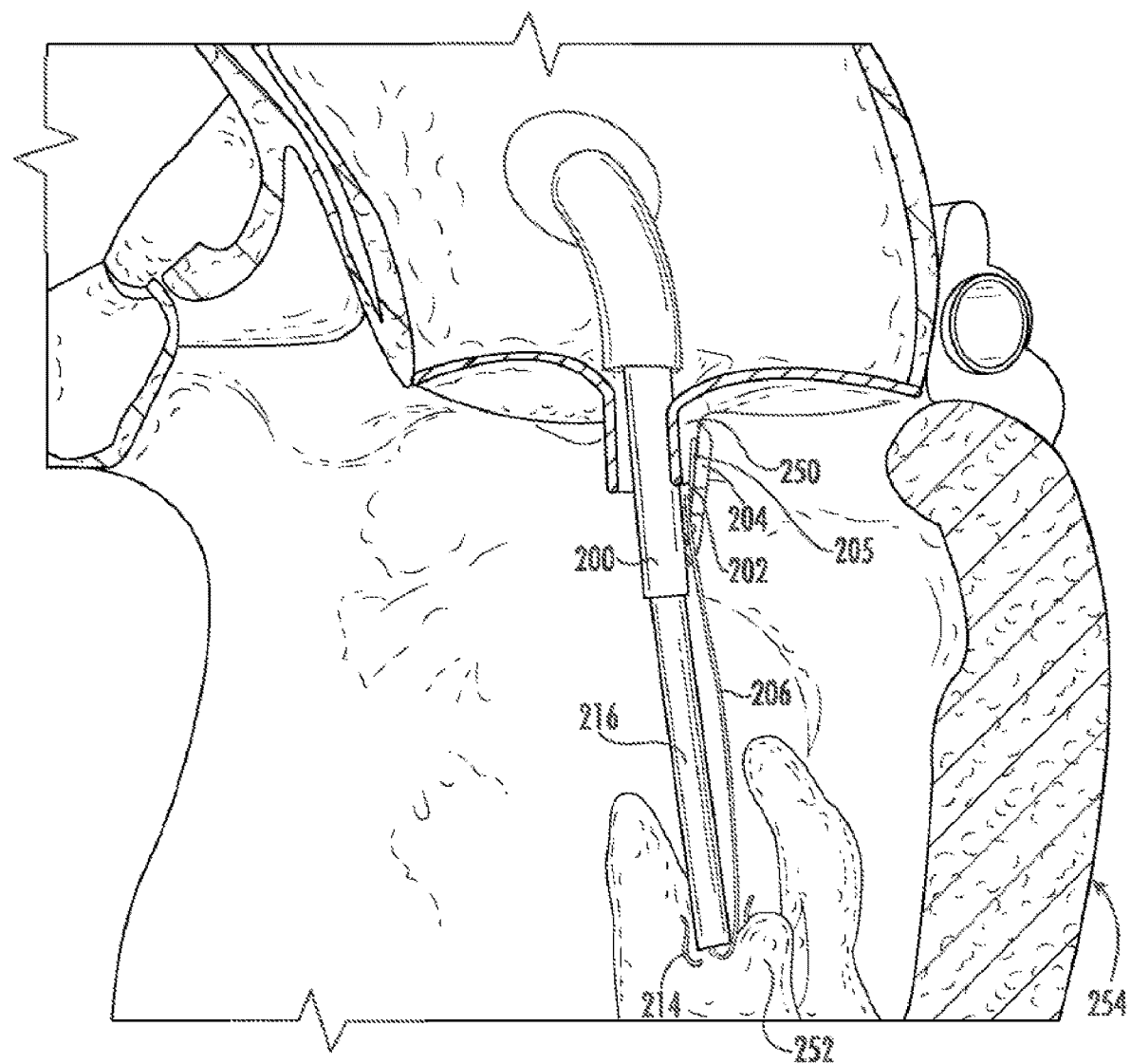
FIG. 2E illustrates a cross-sectional view of the heart of FIGS. 2A-2D with the arms of the anchor deployed.
Figure 2F:
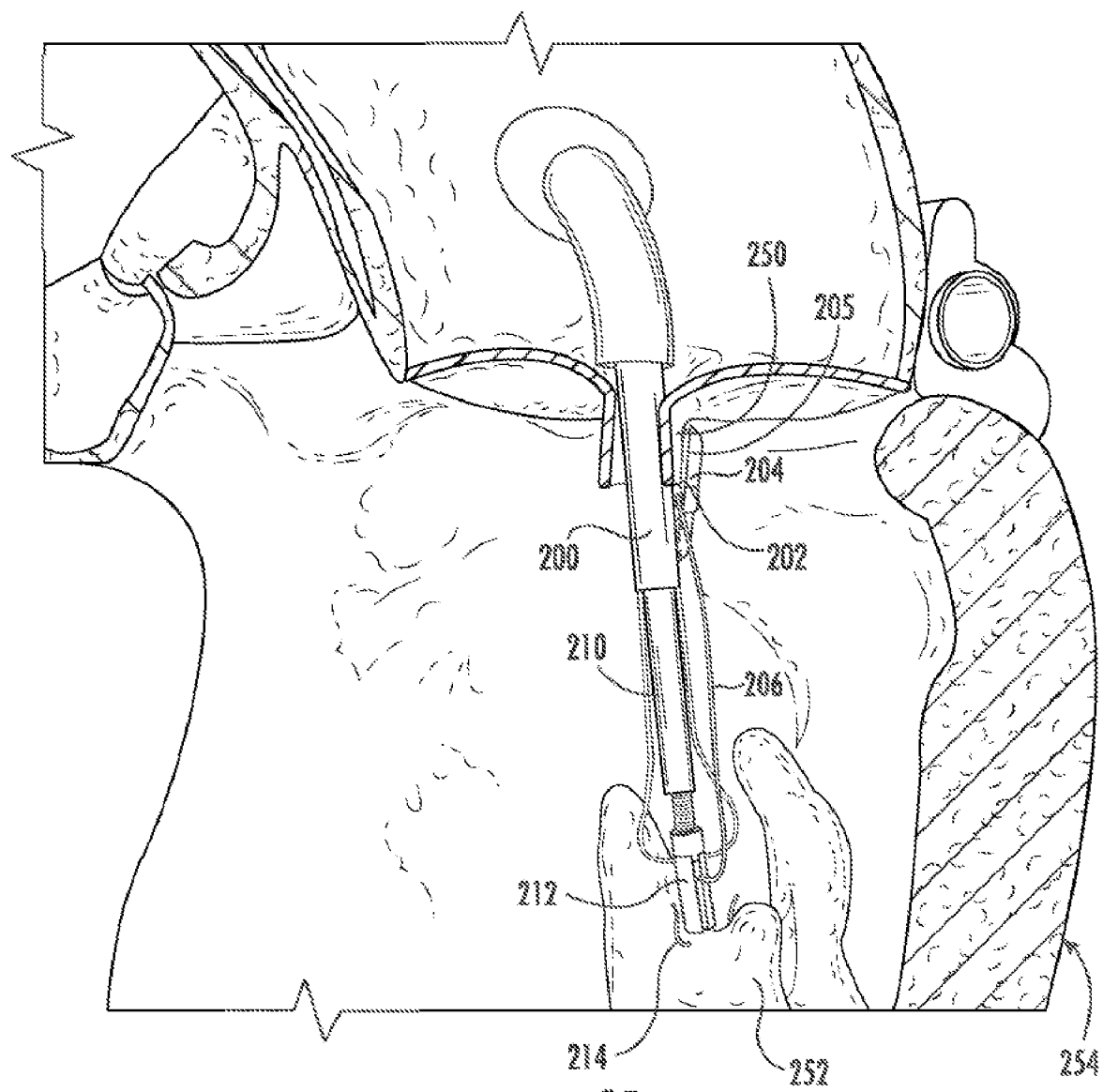
FIG. 2F illustrates a cross-sectional view of the heart of FIGS. 2A-2E with a sheath retracted from the anchor.

With reference to FIGS. 2D-2F, a sheath 216 is shown extended toward a muscle 252 of the heart 254. An anchor catheter 210 having an anchor 212 attached to a distal end of the anchor catheter 210 may be extended through the sheath 216 and toward the muscle 252 of the heart 254. In one embodiment, the sheath 216 restrains one or more arms 214 (e.g., tines) of the anchor 212 in a restrained configuration for delivery. In some embodiments, the arms 214 of the anchor 212 are disposed to extend distally and are configured to engage the heart muscle 252. The arms 214 may be deployed into the muscle 252 by extending the anchor catheter 210 such that the arms 214 extend at least partially out of a distal end of the sheath 216. As the arms 214 extend out of the sheath 216, a shape-memory of the arms 214 biases them to puncture through the muscle 214 and extend proximally as the arms 214 transition from the restrained configuration toward a neutral configuration, as illustrated in FIG. 2D. The anchor 212 and the sheath 216 may be moved further apart from each other (e.g., withdrawing the sheath 216 proximally to expose the anchor catheter 210 and/or advancing the anchor catheter 210 and anchor 212 distally within the sheath 216) such that the arms 214 transition from a deployed configuration to the neutral configuration, as illustrated in FIG. 2E. The anchor 212 and sheath 216 may be moved toward each other (e.g., the sheath 216 may be translated distally and/or the anchor catheter 210 and anchor 212 may be translated proximally) to transition the arms 214 to the restrained configuration once again within the sheath 216 for repositioning and redeployment into another location. With the arms 214 deployed into the muscle 252, the sheath 216 may be further translated proximally away from the anchor 212. The deployed anchor 212 fixed to the muscle 252 further fixes a second end of the artificial chordae tendineae 206 with respect to the muscle 252 that extends into the anchor 212 and proximally into the anchor catheter 210. The artificial chordae tendineae 206 is fixed to the clamp 202 at the first, proximal end and is fixed to the anchor 212 at the second, distal end.

Figure 2G:
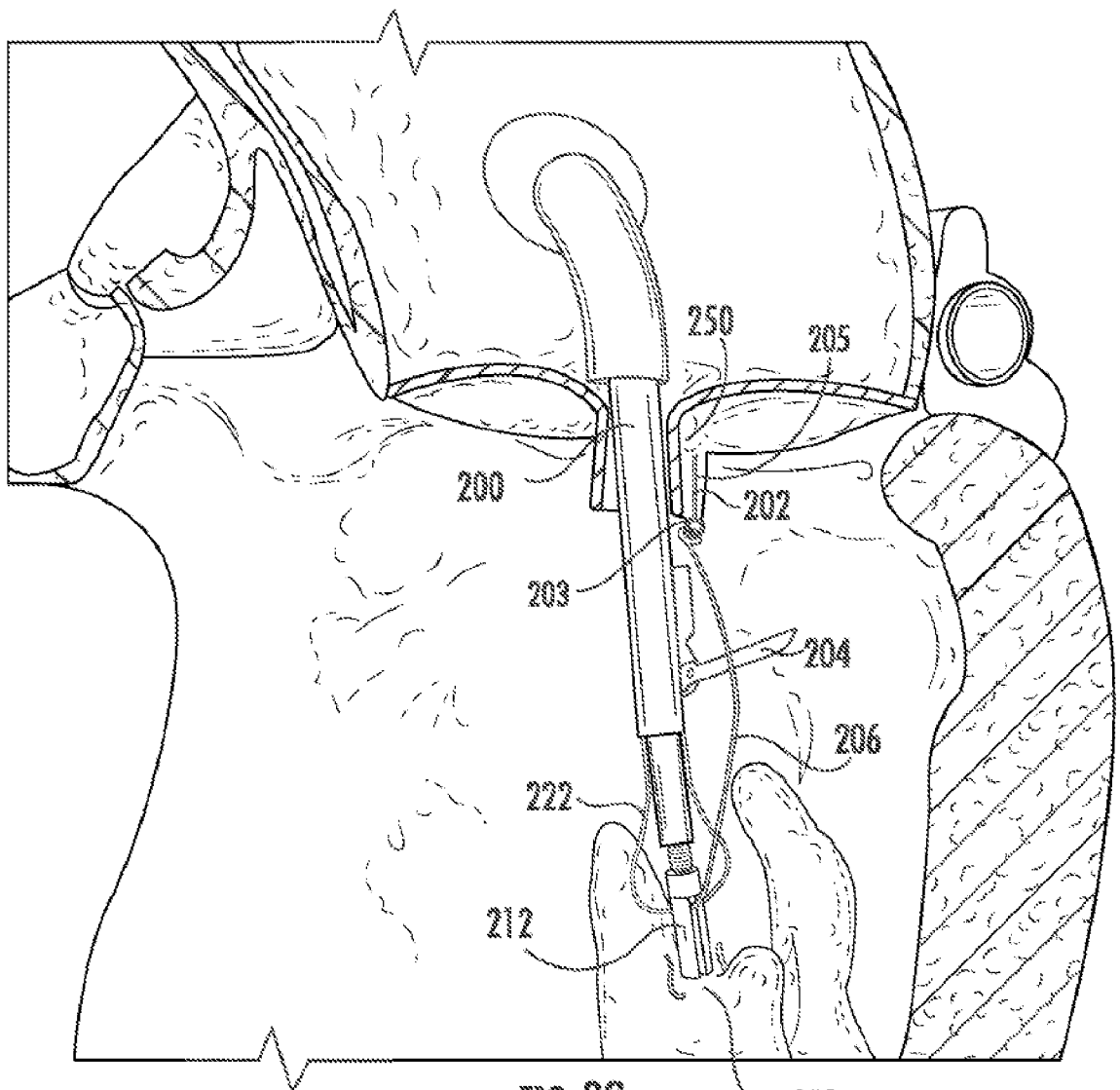
FIG. 2G illustrates a cross-sectional view of the heart of FIGS. 2A-2F with the clamp released onto a leaflet of a valve of the heart.

With reference to FIG. 2G, the clamp 202 in the closed configuration on the leaflet 250 may be released from the spreader 204 by unlocking the clamp 202 from the spreader 204. The clamp 202 may be unlocked from the spreader by removing and/or deactivating a locking mechanism (e.g., a filament extending from a handle of a catheter down through a lumen of the catheter through an aperture corresponding to an arm of a clamp and through a spreader adjacent to the aperture and similarly looped through an aperture corresponding to an opposing arm of the clamp and the spreader and extending proximally through the lumen of the catheter to the handle such that an end of the filament may be pulled on to remove the filament from the system, or locking pins as illustrated and described with respect to FIG. 6 herein). The clamp catheter 200 may be translated distally such that the spreader 204 moves away from the clamp 202 and off of the leaflet 250. The spreader 204 may be translated proximally out of the heart in the open configuration without the clamp 202, of the spreader may have a spring force strong enough to transition the spreader substantially towards to the closed configuration without the spring portion of a clamp 202 before withdrawal. The clamp 202 is fixed to the leaflet 250, fixing the artificial chordae tendineae 206 with respect to the leaflet 250, while the anchor 212 fixates the artificial chordae tendineae with respect to the muscle 252.

In general, a tension of a chordae tendineae between the muscle 252 and the leaflet 204 of a heart affects the function of the valve. Muscle displacement (e.g., papillary muscle) may increase the tension on some of the chords inducing valve functions. Some chords may be substantially insensitive to muscle motion for translating movement from the muscle to the leaflet and may instead or additionally provide structural support for valve leaflet positioning. Chordae tendineae that are too loose may not properly support the attached leaflet or may not properly transfer muscle displacement to the attached leaflet. Chordae tendineae that are too tight may improperly support the attached leaflet, strain, rupture, or transfer an inappropriate and/or insufficient amount of muscle displacement to the attached leaflet. Overtightened chordae tendineae may cause prolapse of another leaflet or may undesirably hold the leaflet substantially open. Overtightening a leaflet in alternative valve treatments may require emergency open heart surgery for repair. However, because the tension of the chordae tendinea in devices described herein are reversible, a medical professional may repair an overtightened leaflet by adjusting the tension in the chordae tendinea.

According to one aspect, the disclosed system allows for replacement and/or adjustment of tension of a chordae tendineae to overcome these problems. The tension and/or length of a chordae tendineae between a leaflet and a muscle (e.g., between a clamp on a leaflet and an anchor in a muscle) may be adjusted to bring the leaflet closer to or farther apart from a muscle. A medical professional may adjust the tension and/or location of devices herein to mimic natural chordae tendineae for heart functions.

In various embodiments, a medical professional may make adjustments in response to visualization of the location of devices in a heart and/or visualization of the functions of the heart (e.g., blood flow). The medical professional may visualize devices in the heart and/or functions of the heart via one or more of transesophageal echocardiography, ultrasound, fluoroscopy, a combination thereof, or the like. Visualization techniques may be used at certain points during a procedure to confirm desirable location of one or more devices and/or anatomies before proceeding with the next step of a procedure. It can be appreciated that the particular adjustments used by the medical professional will vary based on patient characteristics, diseased heart state, etc.

Figure 2H:
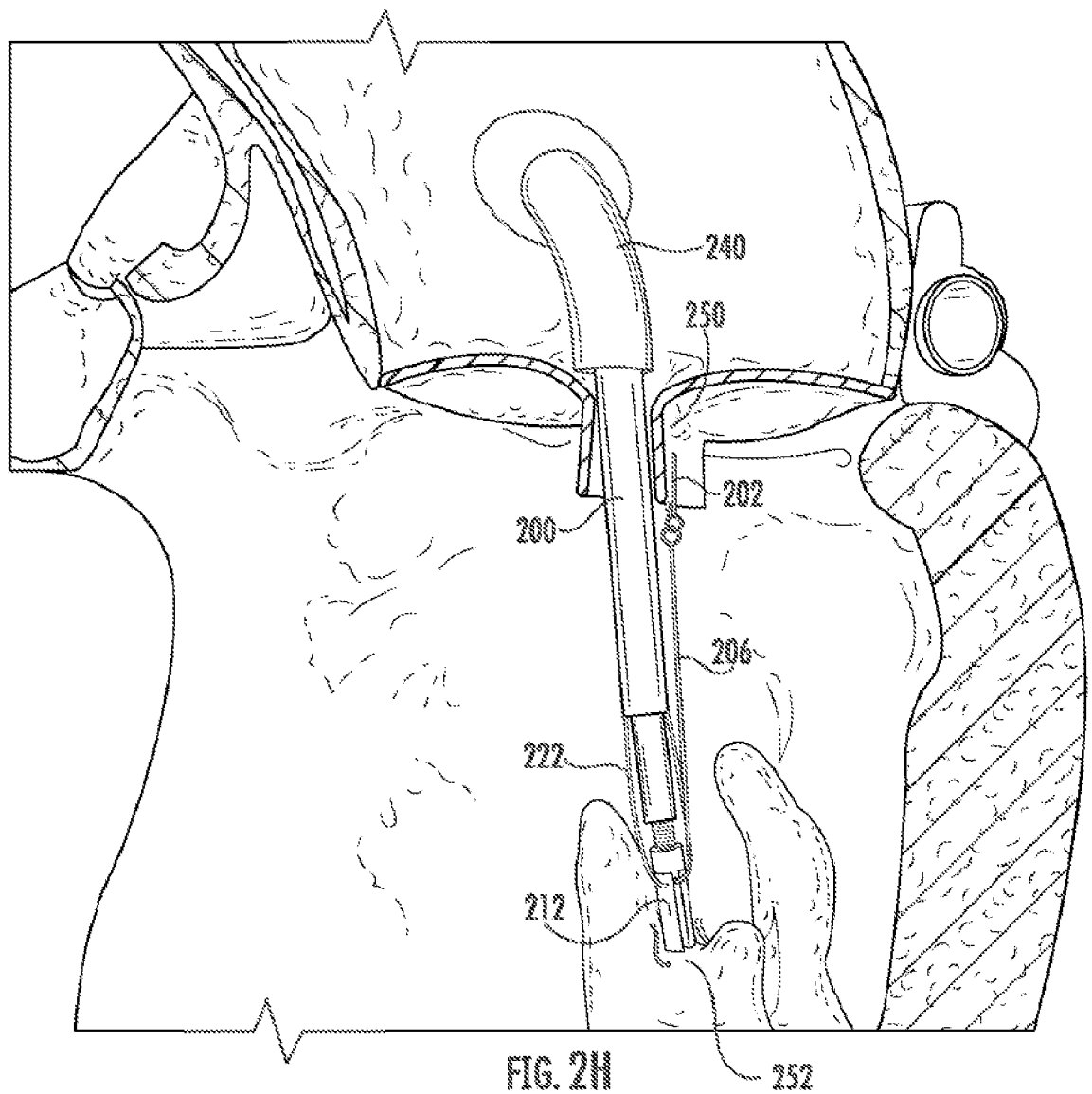
FIG. 2H illustrates a cross-sectional view of the heart of FIGS. 2A-2G and adjusting a tension in the artificial chordae tendineae.
Figure 2I:
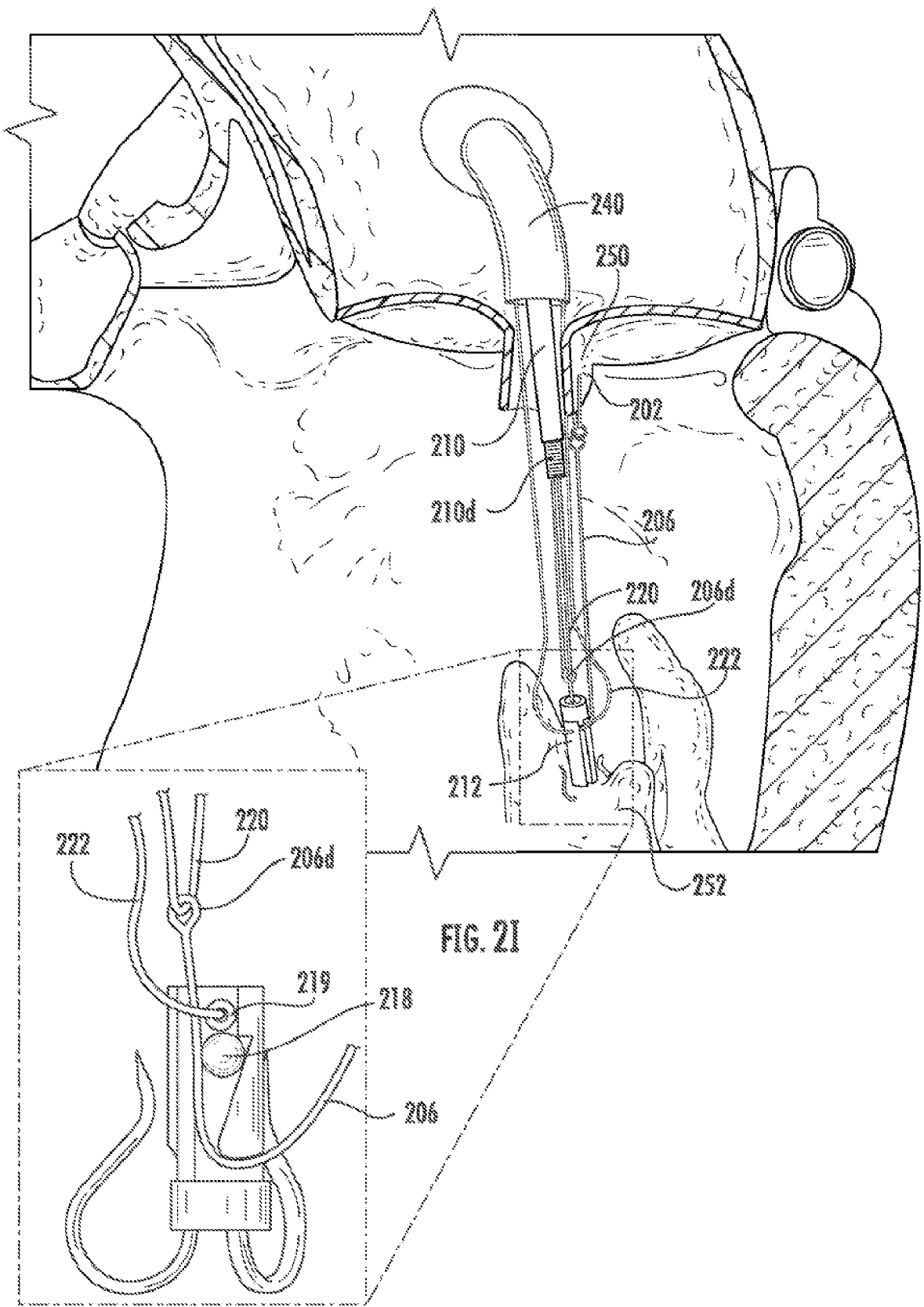
FIG. 2I illustrates a cross-sectional view of the heart of FIGS. 2A-2H with the anchor released from an anchor catheter.
Figure 21:
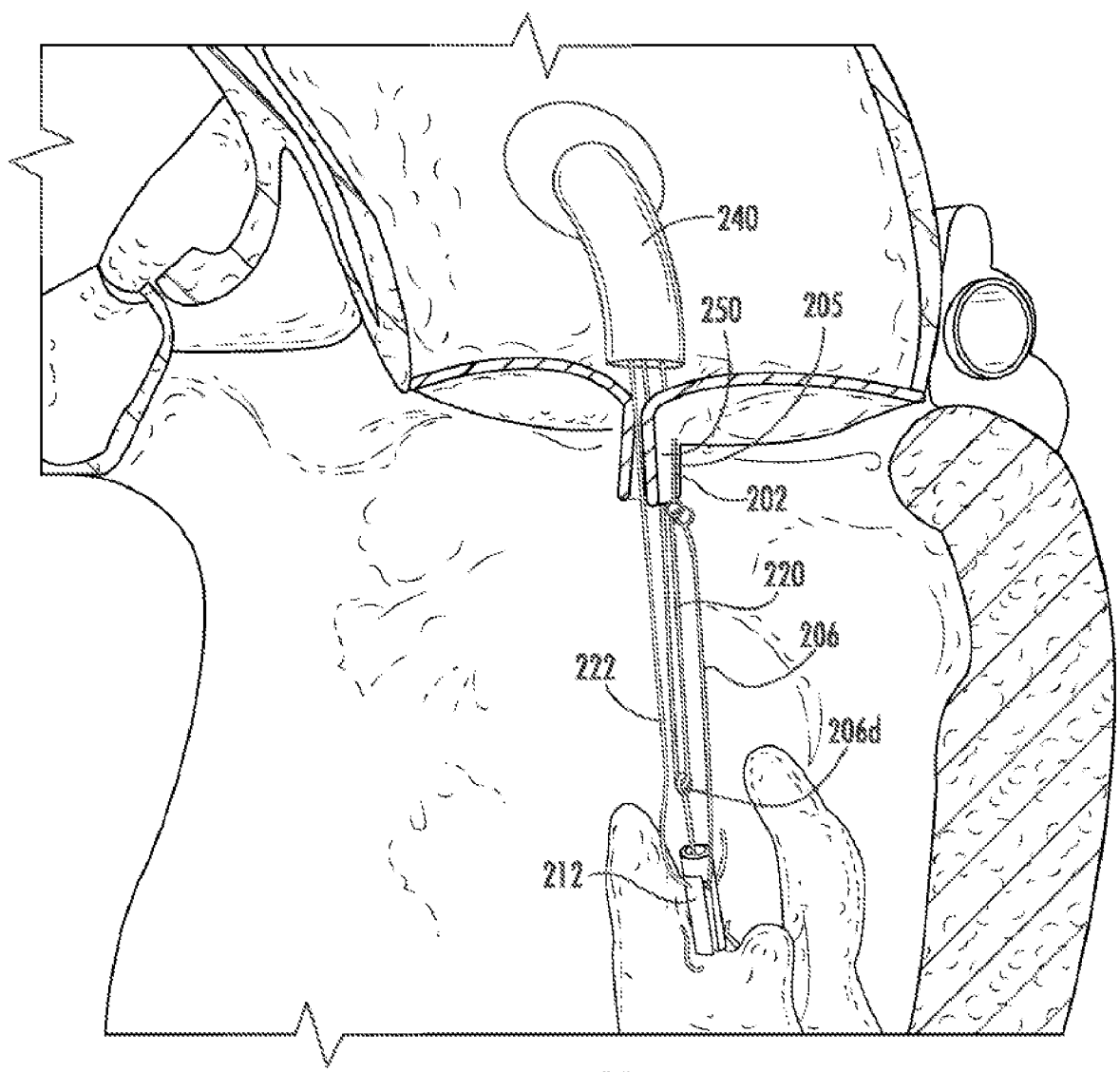

With reference to FIGS. 2H and 2I, a tension in the artificial chordae tendineae 206 may be adjusted to provide an operative valve leaflet 250. The artificial chordae tendineae 206 may be selectively tightened by translating the artificial chordae tendineae 206 through a locking mechanism 218 (e.g., a one-way ratchet) of the anchor 212. The artificial chordae tendineae 206 may be translated through the locking mechanism 218 of the anchor 212 by a tether 220 within the anchor catheter 210 that is coupled to a loop 206d at an end of the artificial chordae tendineae 206.

Proximal translation of the tether 210 pulls on the loop 206d and the artificial chordae tendineae 206 is tightened by the locking mechanism 218 within the anchor 212. The tension of the artificial chordae tendineae 206 may be selectively loosened by releasing at least a portion of the artificial chordae tendineae 206 from the locking mechanism 218 in the anchor 212. The artificial chordae tendineae 206 may be released from the locking mechanism 218 by unlocking the locking mechanism 218 by, for example, relieving the artificial chordae tendineae 206 from the pinching of a one-way ratchet by releasing a roller 219 of the one-way ratchet. The locking mechanism 218 may be unlocked via a proximal translation of a release filament 222 that extends from the delivery catheter 240 (and through the clamp catheter 200 and sheath 216 of FIGS. 2A-2G) and is looped through a release portion of the locking mechanism 218 (e.g., the roller 219 of the one-way ratchet) in the anchor 212. FIG. 2H illustrates the tightened artificial chordae tendineae 206 having a first length extending between the clamp 202 and the anchor 212, that is about to be loosened by the proximal translation of the release filament 222. FIG. 2I illustrates the loosened artificial chordae tendineae 206 having a second length extending between the clamp 202 and the anchor 212 that is longer (i.e., looser) than the first length.

Figure 2K:
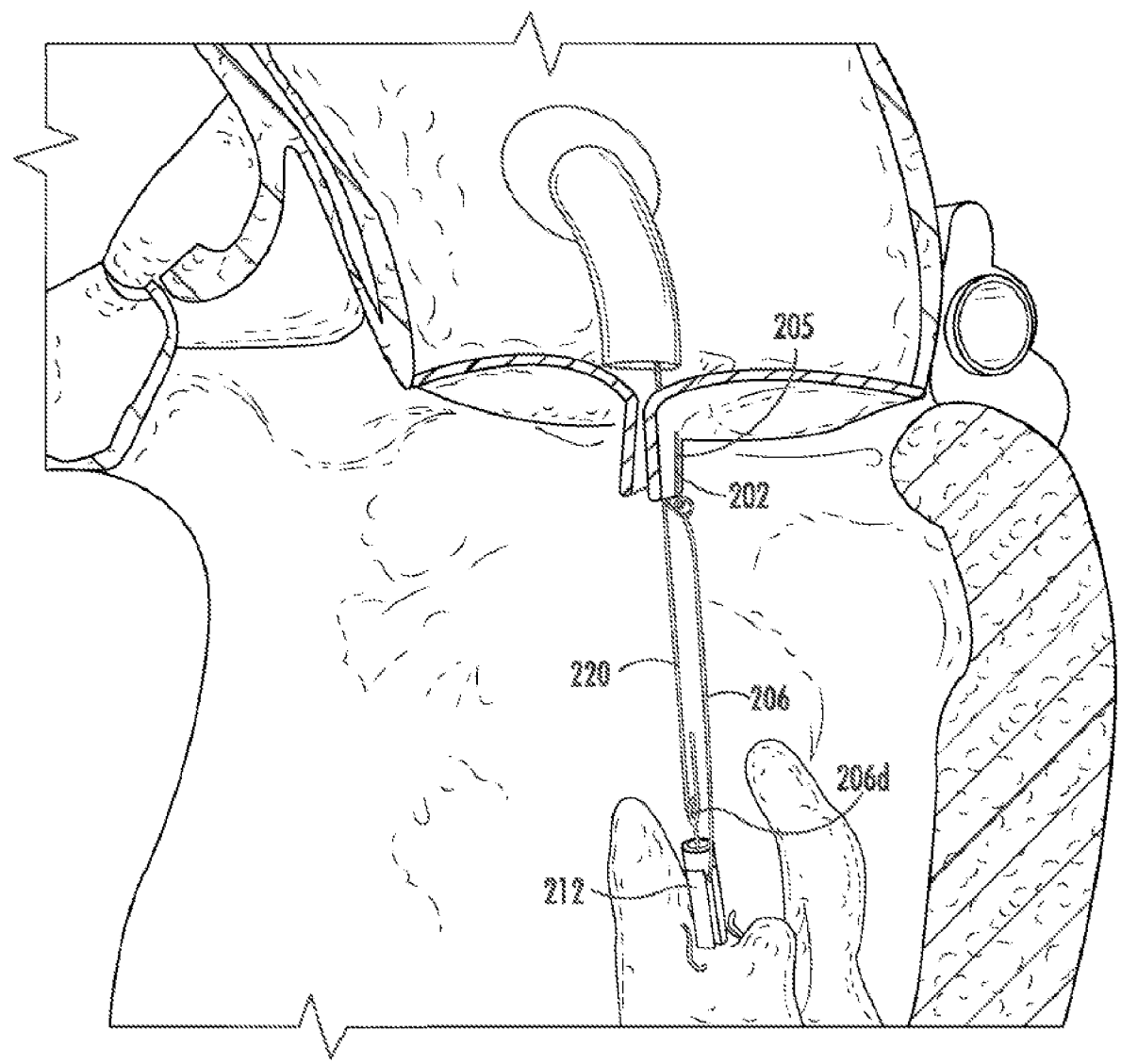
FIG. 2K illustrates a cross-sectional view of the heart of FIGS. 2A-2J and a leash of the artificial chordae tendineae being withdrawn.

With reference to FIGS. 2I-2K, the anchor catheter 210 may be detached from the anchor 212 by unscrewing an engagement portion 210d of the anchor catheter 210 from the anchor 212. Because the anchor 212 is fixed to the muscle 252, the engagement portion 210d may be rotated with respect to the anchor 212 such that the threads of the engagement portion 210d may disengage from corresponding threads within the anchor 212. The anchor catheter 210 may be translated proximally into the delivery catheter 240 after delivering the anchor 212, leaving the tether 220 coupled to the loop 206d of the artificial chordae tendineae 206. Once a desired tension of the length of the artificial chordae tendineae 206 between the clamp 202 and the anchor is achieved, an end of the release filament 222 may be proximally withdrawn such that the release filament 222 is withdrawn from the release portion of the locking mechanism of the anchor 212 without disrupting the release portion (e.g., without further loosening the artificial chordae tendineae 206). Once the desired tension of the length of the artificial chordae tendineae 206 is achieved, an end of the tether 220 may be proximally withdrawn such that the tether 220 is withdrawn from the loop 206d without disrupting the artificial chordae tendineae 206 (e.g., without further tightening the artificial chordae tendineae 206).

Figure 2L:
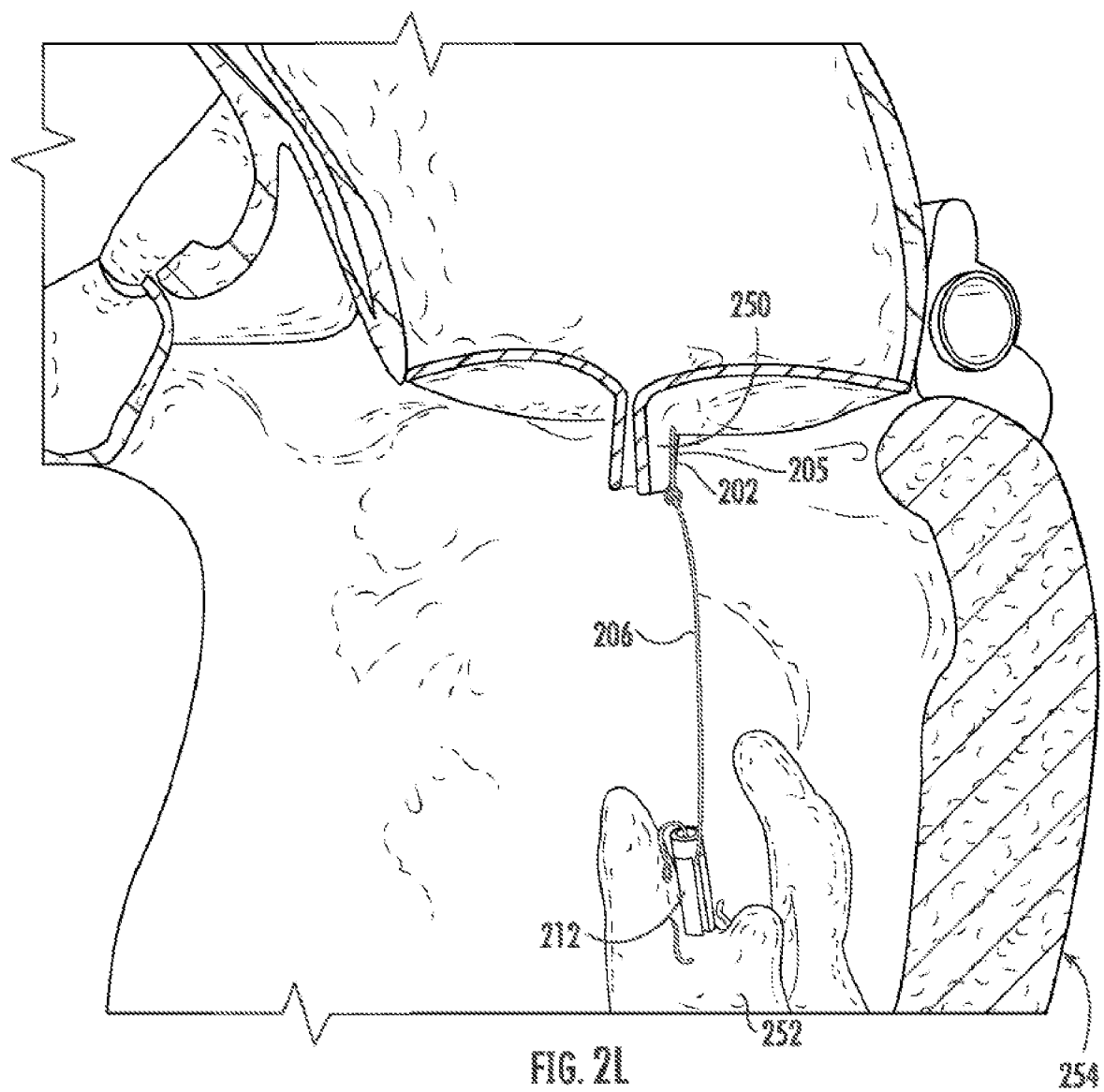
FIG. 2L illustrates a cross-sectional view of the heart of FIGS. 2A-2K with the delivered artificial chordae tendineae.

With reference to FIG. 2L, the catheters and other delivery devices have been removed from the heart 254. In the embodiment of FIG. 2L, a configuration of the artificial chordae tendineae 206, including but not limited to a placement and/or a tension, the artificial chordae tendineae 206 has been adjusted to bring the valves leaflets 250, 251 into an operable configuration so that they appropriately coapt during heart function. The artificial chordae tendineae 206 is shown fixed to the valve leaflet 250 by the clamp 202 and the artificial chordae tendineae 206 is shown fixed to the muscle 252 by the anchor 212. The artificial chordae tendineae 206 has a desirable amount of tension such that it may operate in association with the leaflet 250 and muscle 252 in normal heart functions.

Often, depending upon the diseased state of the heart, it may be desirable to place one or more than one chordae tendineae. The systems disclosed herein enable placement of multiple chordae tendineae without the need to remove the delivery catheter from the heart.

Figure 2M:
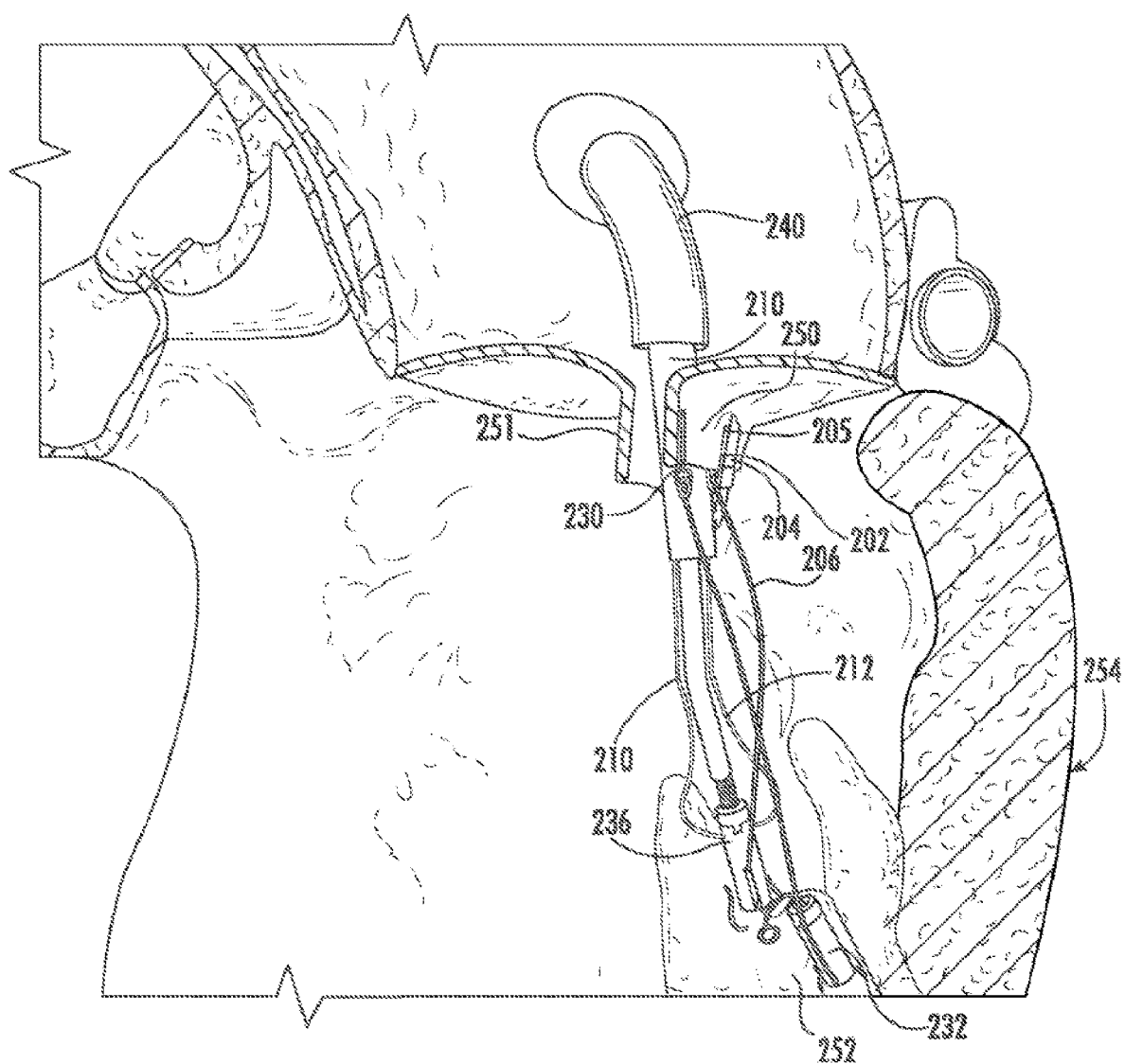
FIG. 2M illustrates a cross-sectional view of the heart of FIGS. 2A-2L with an additional artificial chordae tendineae also being delivered.

With reference to FIGS. 2M and 2N, a second artificial chordae tendineae 236 may be delivered into the heart 252. The second artificial chordae tendineae 236 may be attached at one end to a second clamp 230 and at a second end to a second anchor 232. The second clamp 230 and the second anchor 232 may be delivered to the heart 254 by a separate or reloaded spreader 204 of a clamp catheter 210 and an anchor catheter 210, respectively, by using the same methods described with reference to FIGS. 2A-2L. The second artificial chordae tendineae 236 may be fixed by the second clamp 230 to the same leaflet 250 of the valve, another leaflet 251 of the valve, or another leaflet of another valve. The second artificial chordae tendineae 236 may be fixed by the second anchor 232 to the same muscle 252 or a different muscle of the heart 254.

Figure 3:
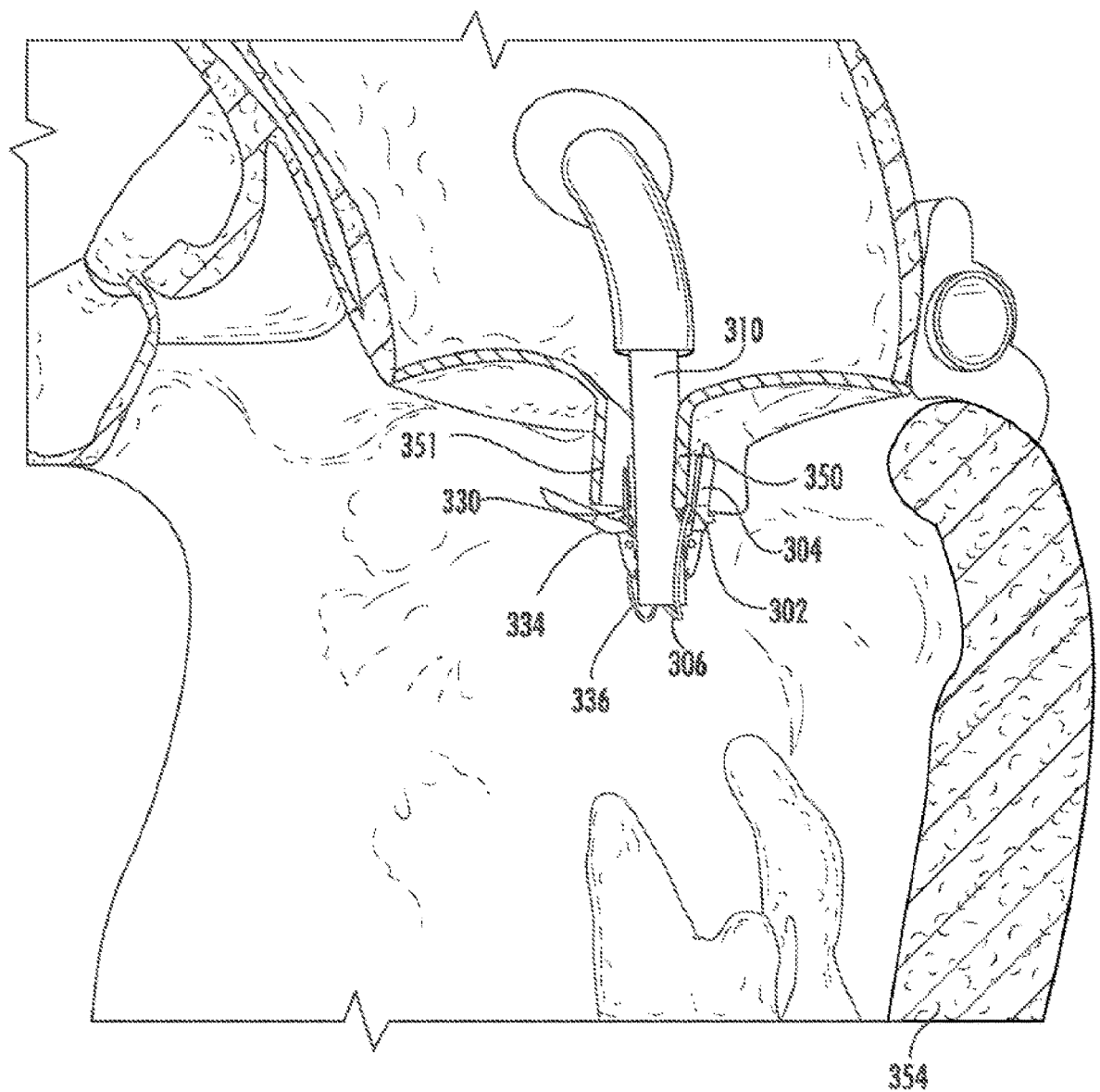
FIG. 3 illustrates a cross-sectional view of a heart with a clamp catheter engaging two leaflets of a valve.

With reference to FIG. 3, a clamp catheter 310 may have a first spreader 304 and a second spreader 334 disposed on a distal end of the clamp catheter containing a first clamp 302 and a second clamp 330, respectively. The first clamp 302 may be coupled to a first artificial chordae tendineae 306 and the second clamp 330 may be coupled to a second artificial chordae tendineae 336. Alternatively, one or both of the clamps 302, 330 may not include artificial chordae tendineae 306, 336 and may be used to temporarily fixate the clamp catheter 310 and/or orient one or both of the leaflets 350, 351 during a procedure. For example, the clamp catheter 310 may be temporarily fixed to one or more leaflets 350, 351 to orient the clamp catheter 310 and/or the leaflets 350, 351 for delivering artificial chordae tendineae 306, 336.

Figure 4A:
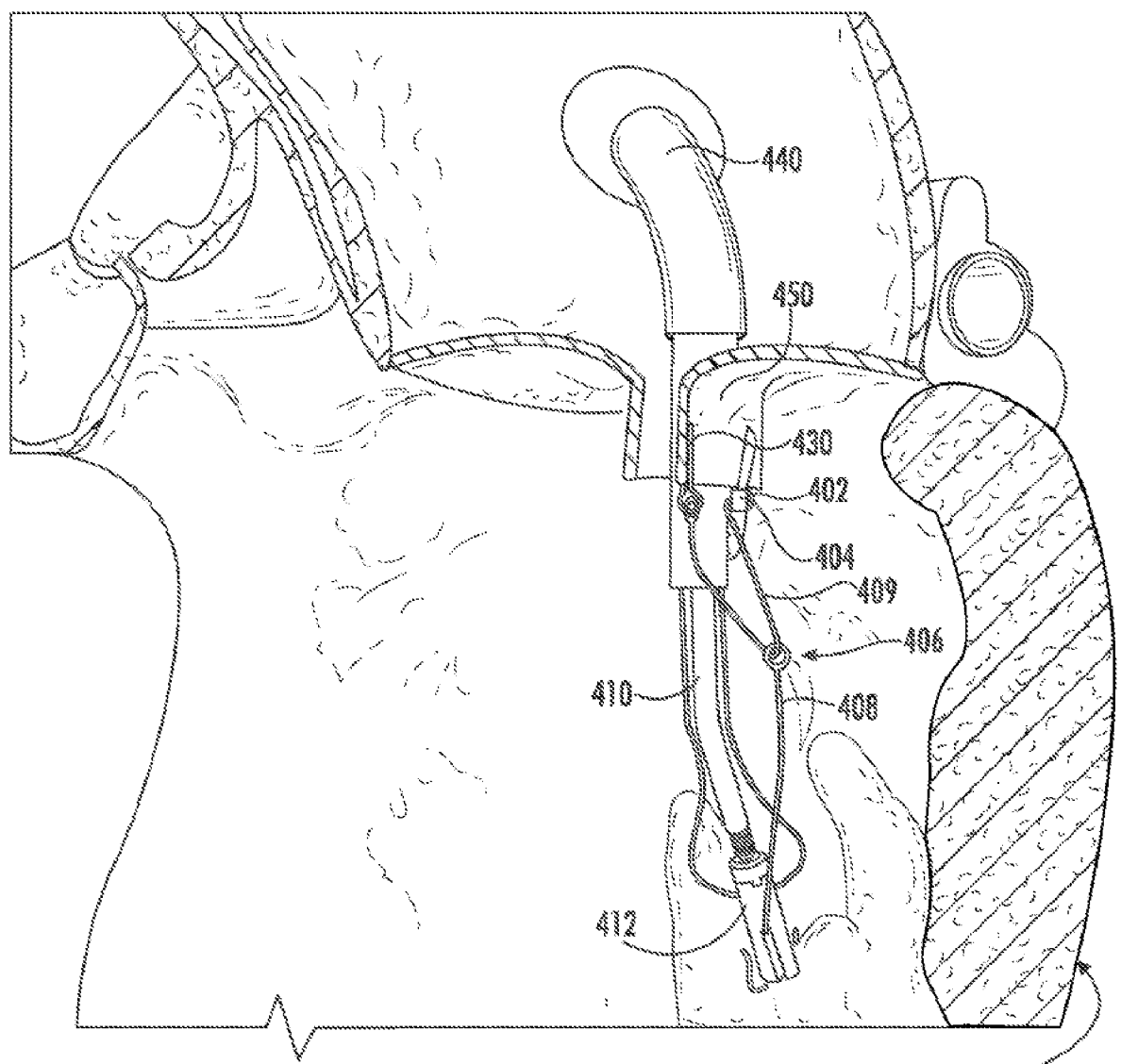
FIG. 4A illustrates a cross-sectional view of a heart and delivering an artificial chordae tendineae having two clamps.
Figure 4B:
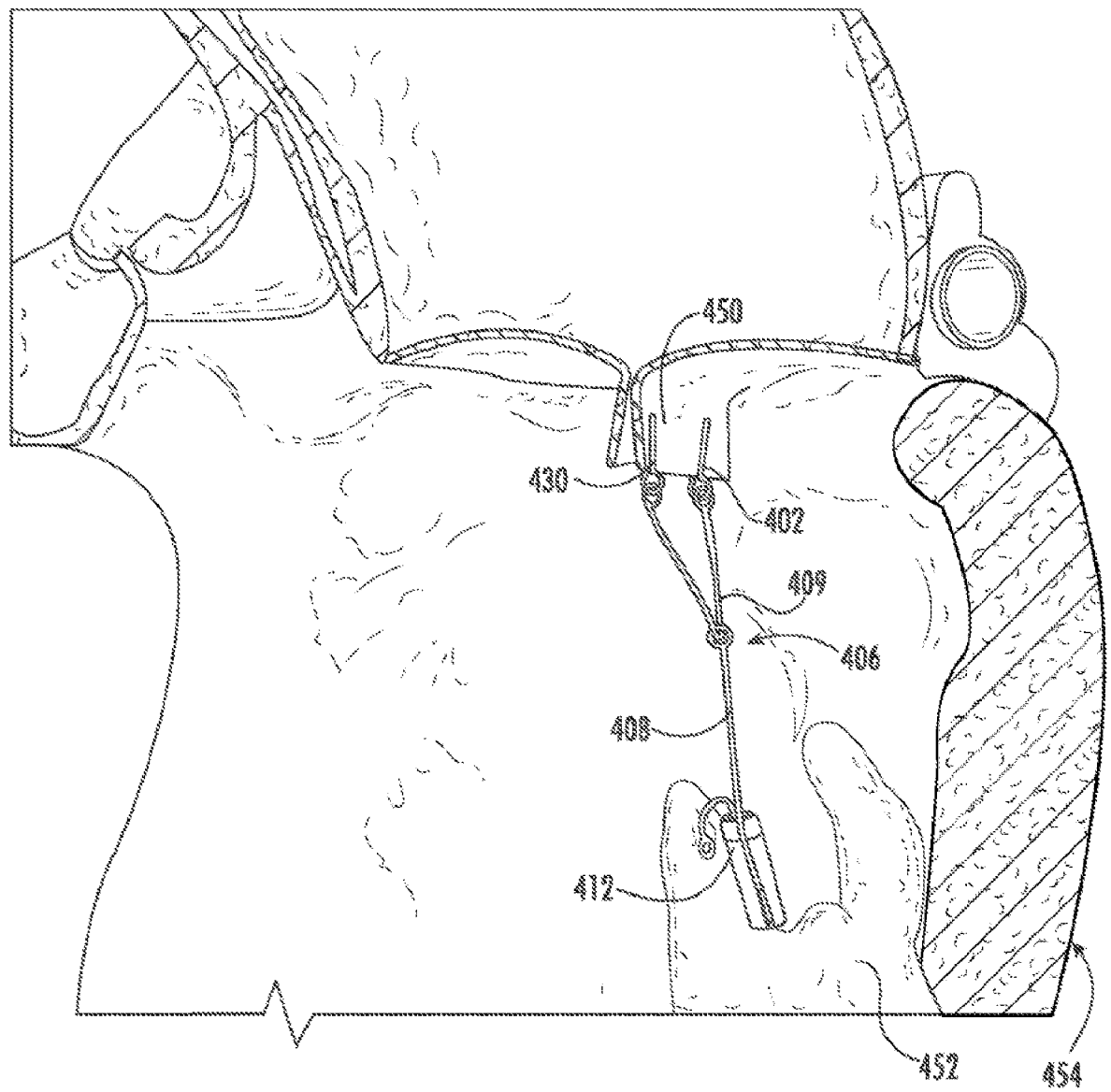
FIG. 4B illustrates a cross-sectional view of the heart of FIG. 4A with the artificial chordae tendineae delivered.
Figure 4C:
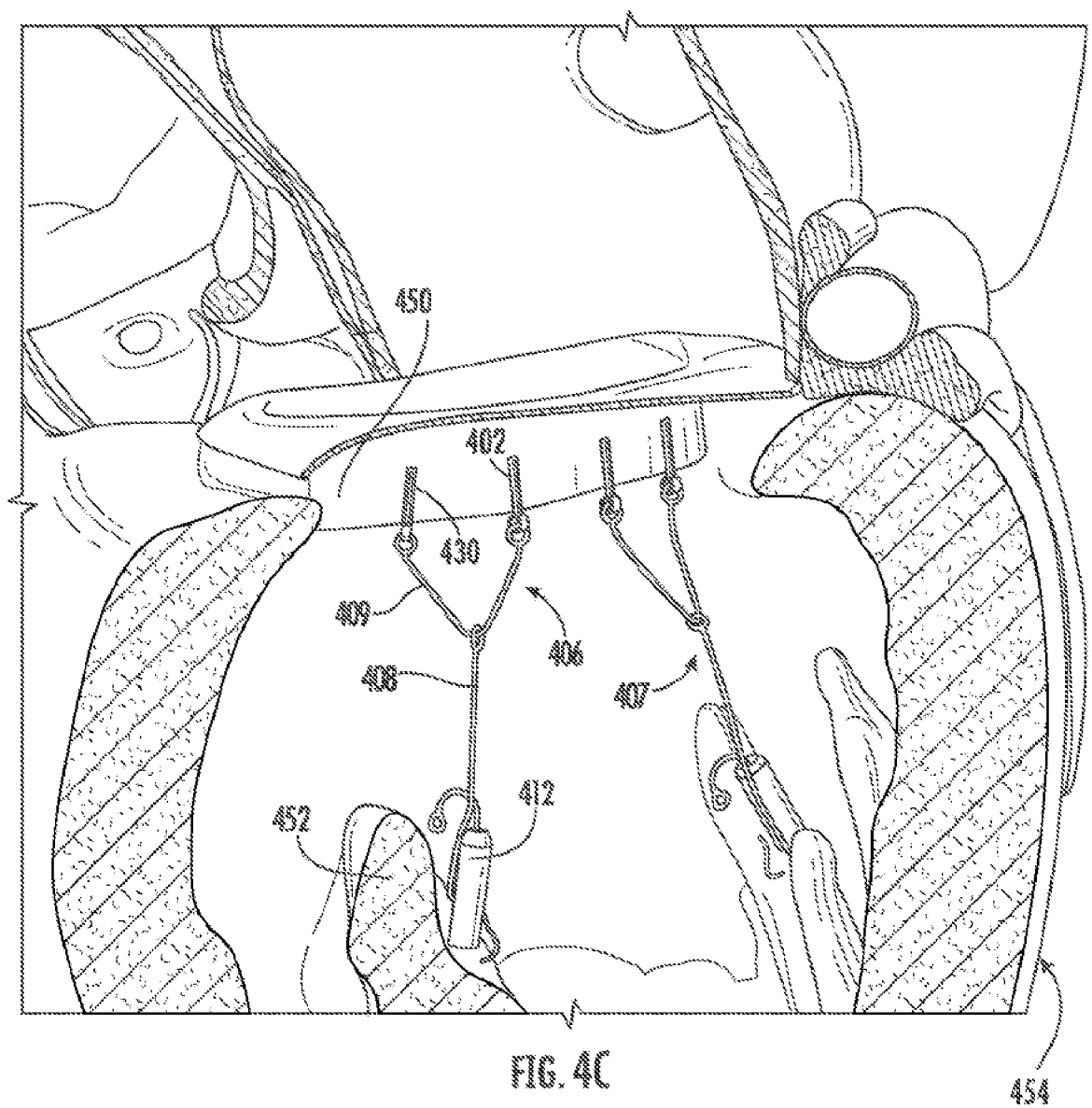
FIG. 4C illustrates a cross-sectional view of the heart of FIGS. 4A and 4B with an additional artificial chordae tendineae having two clamps.

With reference to FIGS. 4A-4C, a first artificial chordae tendineae 406 may be delivered into a heart 454 that is made up of a first filament 408 and a second filament 409 that are coupled to each other. The second filament is coupled at each end to a first clamp 402 and a second clamp 430. The first filament 408 is coupled to an anchor 412 at one end and the first filament is coupled to the second filament 409 at a second end such the second end may freely slide along the length of the second filament 409. The artificial chordae tendineae 406 may be pre-loaded within a delivery catheter 440 with the first filament 408 and second filament 409 coupled to each other. A spreader 404 may deliver the clamps 402, 430 and an anchor catheter 410 may deliver the anchor 412. The first filament 408 may pull on each of the clamps 402, 430 with substantially equal force because the first filament 408 may freely slide along the second filament 409 to a mid-portion of the second filament 409, transferring the force from the first filament 408 substantially equally to the clamps 402, 430. A medical professional may selectively adjust the length and tension of the first filament 408 and the second filament 409 for proper heart function. The medical professional may additionally adjust the distance between the clamps 402, 430 along a leaflet 450 for proper heart function. A second artificial chordae tendineae 407 may also be similarly delivered onto the same leaflet 450, a different leaflet, the same muscle 452, or a different muscle.

Figure 5A:
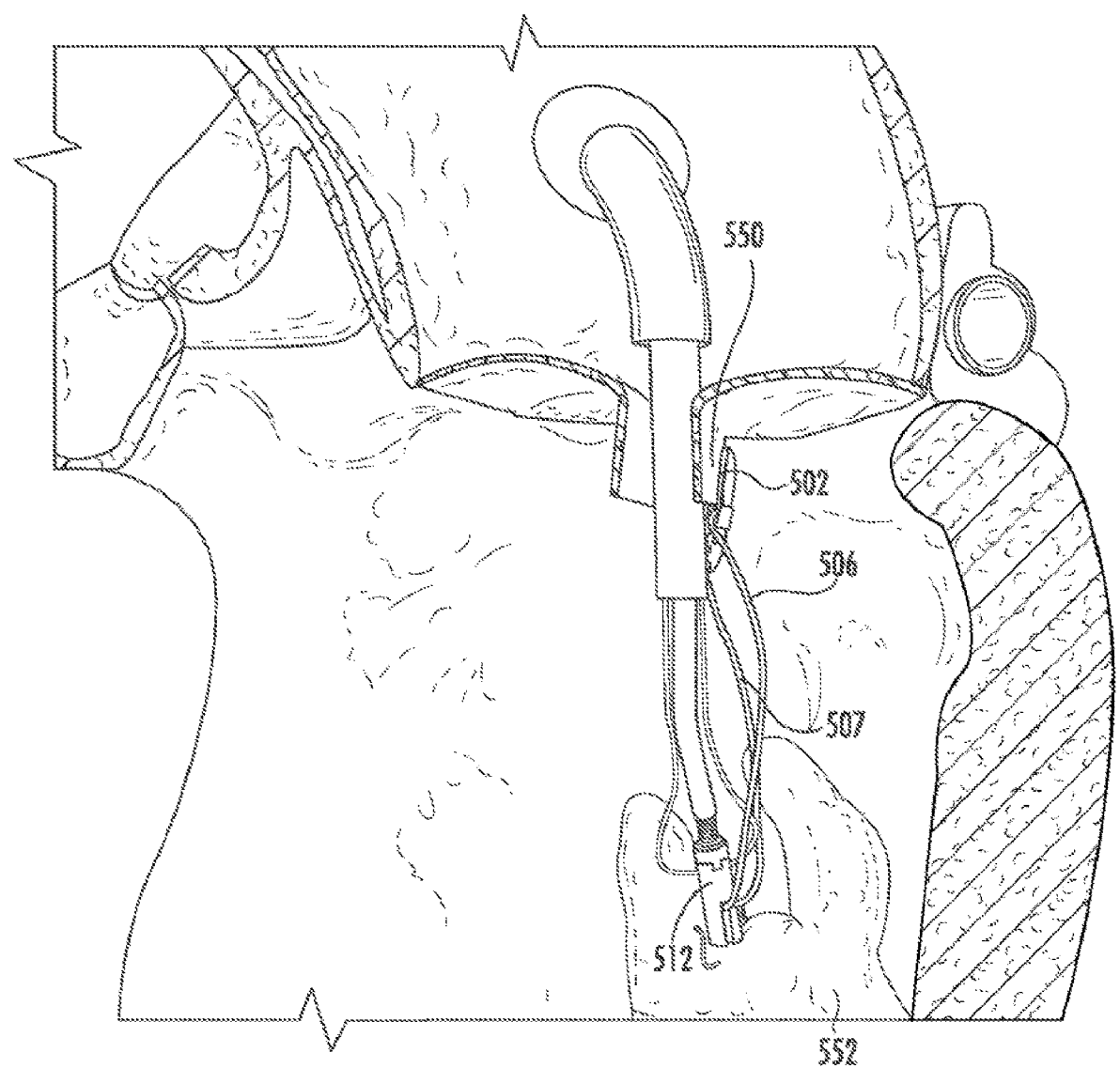
FIG. 5A illustrates a cross-sectional view of a heart and delivering an artificial chordae tendineae having two chords.
Figure 5B:
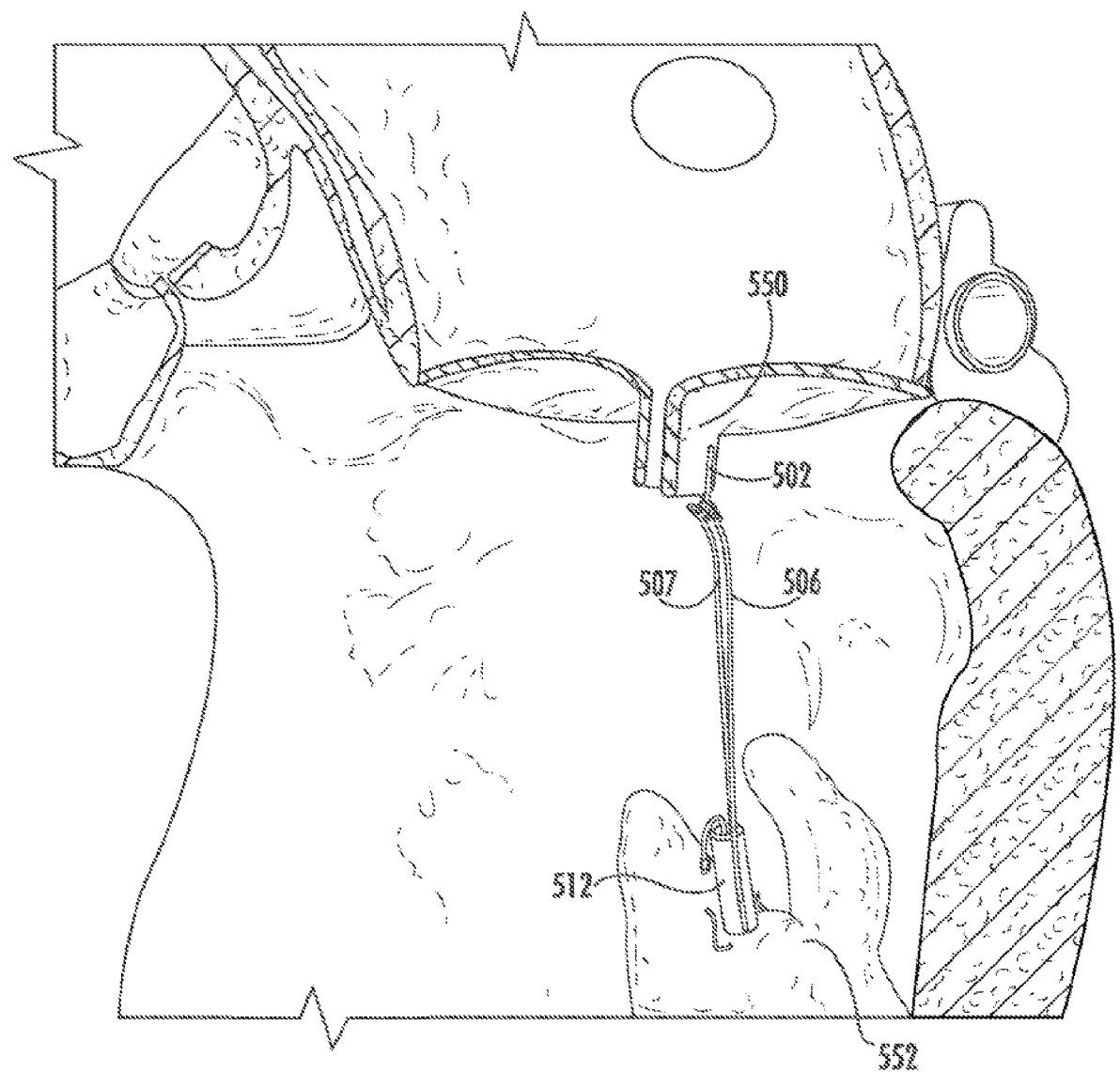
FIG. 5B illustrates a cross-sectional view of the heart of FIG. 5A with the artificial chordae tendineae having two chords delivered.

With reference to FIGS. 5A and 5B, a clamp 502 and associated anchor 512 may be coupled to a first artificial chordae tendineae 506 and to a second artificial chordae tendineae 507. Such a system may be delivered with both artificial chordae tendineae 506, 507 pre-coupled to the clamp 502 and the anchor 512. A tension of each artificial chordae tendineae 506, 507 may be independently and selectively adjusted by a professional operating a locking mechanism of the anchor 512. A second artificial chordae tendineae 507 may supplement and strengthen the transfer of forces from a muscle 552 to a leaflet 550 and/or add additional support in case a delivered device fails.

With reference to FIG. 6, a clamp 600 with a spreader 620 that is disposed on a catheter 634 may be used with a system embodiment described herein. The clamp 600, with arms 602 and a spring portion 604, is illustrated in an open configuration. The spring portion 604 biases the arms 602 to the closed configuration. The spreader 620 may be releasably coupled to the clamp 600. The spreader 620 may transition the clamp 600 between the closed configuration and the open configuration. The spreader 620 includes a base 622 with a first pin 624 extending from the base 622. A lever 626 may be rotatably disposed about the first pin 624. The base 622 includes a first channel 641 and the lever 626 includes a second channel 642 that are each configured to accept an arm 602 of the clamp 600. The ends of each arm 602 include an aperture 608. Each aperture 608 has a central axis that extends substantially along each of the arms 602 and is configured to accept one of two locking pins 610. One locking pin 610 extends through the first channel 641 and into the aperture 608 of an arm 602, while the other locking pin 610 extends through the second channel 642 and into the aperture 608 of the opposing arm 602. The locking pins 610 fix the arms 602 to the base 622 and the lever 626 such that the spreader 620 can manipulate the arms 602 between the open and closed configurations and so that the clamp 600 cannot be released from the spreader 620. Because the arms 602 are locked within the channels 641, 642, the arms 602 may transition between the closed configuration and the open configuration with a movement of the lever 626. The lever 626 may move about the first pin 624 via translation of a first filament 630 that may be coupled to a slot 632 of the lever 626. As the lever 626 rotates about the first pin 624, it also moves the arm 602 that is within the second channel 642 while the opposing arm 602 is fixed within the first channel 641 of the base 622. In some embodiments, the pins 610 may extend through a third and a fourth aperture in each of the base 622 and the lever 626 rather than the first and second channels 641, 642, while still extending into the apertures 608. A second filament 612 may be coupled at each end to the locking pins 610 such that the second filament 612 may be grasped and pulled such that the locking pins 610 are removed from the apertures 608 and channels 641, 642, thereby releasing the arms 602 from the base 622 and the lever 626. FIG. 6 illustrates the base 622 of the spreader 620 adhered to a distal end of a catheter 634. The first filament 630 extends proximally into the catheter 634 to be manipulated by a medical professional. Because the base 620 is coupled to the catheter 634, the catheter 634 may be inserted into a patient to a target location to deliver the clamp 600. Also, because the base 622 is fixed to the catheter 634, as the first filament 630 manipulates the lever 626 containing an arm 602, the lever 626 works against the bias of the spring portion 604 and moves the clamp 600 from the closed configuration to the open configuration by moving the arm 602 in the lever 626 away from the fixed arm 602 in the base 622.

Still referring to FIG. 6, an embodiment of a method according to the present disclosure may include inserting the catheter 634 toward a valve (e.g., through the valve). In some embodiments, the catheter 634 may include the spreader 620 disposed on a distal end of the catheter 634, which may be reversibly coupled to the clamp 600 in a closed configuration for navigating through the patient and/ or a working channel. Once the catheter 634 is near the target site of the valve, the clamp 600 may be transitioned to the open configuration by pulling proximally on the first filament 630 coupled to the lever 626 and holding tension on the first filament 630. The lever 626 rotates about the first pin 624 and moves an arm 602 within the lever 626 apart from the opposing arm 602 in the base 622. With the clamp 600 in the open configuration, the catheter 634 may move the clamp into position proximate a leaflet (e.g., about a flailing leaflet) of the valve such that an arm 602 is on either side of the leaflet (e.g., see FIG. 2C and discussion above). With the clamp 600 in position about the leaflet, tension may be released on the first filament 630, allowing the biased spring portion 604 of the clamp 600 to transition the clamp 600 into the closed configuration about the leaflet. The medical professional may optionally re-open the spreader 620 and clamp 600 by again pulling proximally on the first filament 630 to reposition the clamp 600 if desired. Repositioning the clamp 600 may be desirable, e.g., if accidentally released, if a better position is realized after deploying the clamp 600, or to configure a tension in an artificial chordae tendineae attached to the clamp 600. Once the clamp 600 is in position, the second filament 612 attached to the locking pins 610 may be pulled (e.g., by a grasper, a third filament, or the like) such that the pins 610 are removed from the apertures 608 of the arms 602. With the pins 610 removed, the clamp is no longer fixed to the spreader 620 and the spreader 620 releases the clamp 600. The clamp 600 may be left delivered on the leaflet, and the catheter 634 and spreader 620 may be withdrawn from the patient. Additionally or in the alternative, a clamp may be delivered with a fourth filament (e.g., artificial chordae tendineae) that may extend from the clamp 600 (e.g., from the spring portion 604) to another device (e.g., an anchor) to be used in a medical treatment (e.g., anchoring artificial chordae tendineae to a leaflet and to a ventricle or a papillary muscle). Subsequent valve repair treatments may include transcatheter valve replacement, whereas alternative valve repair treatments may only be further repaired via, e.g., open heart valve replacement.

In various embodiments, one or more catheters, sheaths, and/or filaments may be translated through a body of the patient and/or through each other. One or more of these parts of the system may be connected to a handle. A medical professional may translate one or more of these parts proximally and/or distally with respect to the handle. The handle may be connected to one or more of these parts by one or more pulleys for translating the parts. The medical professional may hold and/or lock one or more parts such that it is fixed with respect to other parts, while one or more of the other parts is translated proximally or distally. Devices herein may be steered and delivered through the femoral vein and septal wall using an outer delivery sheath that may be, e.g., about 24 to about 30 french and may remain in place during multiple therapies, e.g., reducing the annulus of a mitral valve and subsequently deliver chordae tendinea.

In various embodiments of the present disclosure, one or more arms of a clamp may have locking features for use with a device that may transition the clamp between a closed configuration and an open configuration. The locking features may include apertures, edges for channels, tabs, or the like. These locking features may be engaged by additional devices such as locking pins, channels, clamps, or the like. The additional devices may engage the locking features to transition the clamp between the closed and open configurations and the additional devices may disengage the locking features to deliver the clamp from one or more devices into a patient.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A system for delivering a chordae tendineae into a heart of a patient, the system comprising:
    a delivery catheter;
    a clamp catheter configured to translate through the delivery catheter;
    a spreader disposed on the clamp catheter;
    a first clamp at least partially contained in the spreader in a closed configuration, the first clamp being attached to a first end of the chordae tendineae;
    an anchor catheter configured to translate through the delivery catheter, the anchor catheter having an anchor attached to a second end of the chordae tendineae; and
    a sheath extended over the anchor catheter and anchor, the sheath configured to restrain an arm of the anchor.

2. The system of claim 1, wherein the second end of the chordae tendineae extends through a ratchet of the anchor and the second end of the chordae tendineae is coupled to a tether extending through the anchor catheter, the tether configured to increase a tension in the chordae tendineae via a translation of the tether.

3. The system of claim 2, further comprising a release filament that extends through a release roller of the ratchet, the release filament configured to unlock the chordae tendineae from the ratchet via translation of the release filament.

4. The system of claim 1, wherein the first clamp is reversibly locked to the spreader.

5. The system of claim 1, further comprising a second clamp attached to the first clamp by a clamp filament, the clamp filament being slidably coupled to the first end of the chordae tendineae.

6. The system of claim 1, wherein the anchor catheter and sheath extend through the clamp catheter.

7. A method of delivering a chordae tendineae into a heart of a patient, the method comprising:
    transluminally inserting a delivery catheter into the heart;
    extending a clamp catheter through the delivery catheter, the clamp catheter having a spreader containing a clamp in a closed configuration, the clamp being attached to a first end of the chordae tendineae;
    manipulating the spreader to transition the clamp from the closed configuration to an open configuration;
    positioning the clamp adjacent a leaflet of a valve of the heart;
    manipulating the spreader to transition the clamp from the open configuration to the closed configuration onto the leaflet;
    extending a sheath through the delivery catheter towards a tissue of the heart;
    extending an anchor catheter having an anchor, the anchor being attached to a second end of the chordae tendineae at a distal end of the anchor catheter through the sheath; and
    driving the anchor into the tissue.

8. The method of claim 7, further comprising observing regurgitation of the valve via transesophageal echocardiogram or fluoroscopy and adjusting a tension in the chordae tendineae.

9. The method of claim 7, further comprising adjusting a tension in the chordae tendineae by selectively translating the chordae tendineae through a ratchet of the anchor and selectively releasing the chordae tendineae from the ratchet.

10. The method of claim 7, further comprising deploying the clamp from the spreader by removing a plurality of pins from the clamp and spreader.

11. The method of claim 7, wherein manipulating the spreader is performed by translating a spreader filament proximally through the clamp catheter.

12. The method of claim 7, further comprising repositioning the clamp by transitioning the clamp from the closed configuration to the open configuration, moving the clamp from a first portion of the leaflet to a second portion of the leaflet, and transitioning the clamp from the open configuration to the closed configuration onto the leaflet.

13. The method of claim 7, wherein extending a sheath through the delivery catheter is extended through the clamp catheter.

14. The method of claim 7, wherein driving the anchor further comprises deploying an arm from the anchor by extending the anchor catheter such that the arm extends at least partially out of a distal end of the sheath.

15. The method of claim 7, further comprising repositioning the anchor by extending the anchor catheter proximally through the sheath from a first portion of the tissue and extending the anchor catheter to a second portion of the tissue.

16. The method of claim 7, further comprising removing the clamp catheter, the sheath, the anchor catheter, and the delivery catheter from the patient.

17. A method of delivering a chordae tendineae into a heart of a patient, the method comprising:
    delivering a clamp on a clamp spreader to a leaflet of a heart valve, the clamp being attached to a first end of the chordae tendineae;
    manipulating the clamp spreader to deploy the clamp on the heart valve leaflet;
    delivering an anchor into a muscle of the heart, the anchor being attached to a second end of chordae tendineae; and
    adjusting a tension in the chordae tendineae.

18. The method of claim 17, wherein delivering the clamp further comprises manipulating the spreader to transition the clamp from a closed configuration to an open configuration, positioning the clamp adjacent the leaflet, and manipulating the spreader to transition the clamp from the open configuration to the closed configuration onto the leaflet.

19. The method of claim 17, wherein delivering the anchor further comprises deploying a plurality of arms into the muscle from the anchor by extending the anchor such that the arms extend at least partially out of a distal end of a sheath.

20. The method of claim 17, further comprising observing regurgitation of the heart valve via transesophageal echocardiogram or fluoroscopy.

* * * * *